United States Patent
Xu et al.

(10) Patent No.: US 12,303,263 B2
(45) Date of Patent: May 20, 2025

(54) NON-INVASIVE DETECTION METHOD, DEVICE, SYSTEM AND WEARABLE APPARATUS FOR TISSUE ELEMENT

(71) Applicant: Tianjin Sunrise Technologies Development Co., Ltd., Tianjin (CN)

(72) Inventors: Kexin Xu, Tianjin (CN); Tongshuai Han, Tianjin (CN); Yuxiang Wang, Tianjin (CN); Picheng Zhao, Tianjin (CN)

(73) Assignee: Tianjin Sunrise Technologies Development Co., Ltd., Tianjin (CN)

( * ) Notice: Subject to any disclaimer, the term of this patent is extended or adjusted under 35 U.S.C. 154(b) by 1015 days.

(21) Appl. No.: 17/312,818

(22) PCT Filed: Dec. 16, 2019

(86) PCT No.: PCT/CN2019/125781
§ 371 (c)(1),
(2) Date: Jun. 10, 2021

(87) PCT Pub. No.: WO2020/119825
PCT Pub. Date: Jun. 18, 2020

(65) Prior Publication Data
US 2022/0054051 A1    Feb. 24, 2022

(30) Foreign Application Priority Data
Dec. 14, 2018 (CN) .......................... 201811539082.1

(51) Int. Cl.
*A61B 5/1455*    (2006.01)
*A61B 5/00*      (2006.01)

(52) U.S. Cl.
CPC ............ *A61B 5/1455* (2013.01); *A61B 5/681* (2013.01); *A61B 2562/0238* (2013.01); *A61B 2562/185* (2013.01)

(58) Field of Classification Search
CPC ... A61B 5/1455; A61B 5/14552; A61B 5/681; A61B 2562/0238; A61B 2562/185
See application file for complete search history.

(56) References Cited

U.S. PATENT DOCUMENTS 5,655,530 A    8/1997  Messerschmidt
5,823,951 A    10/1998 Messerschmidt
(Continued)

FOREIGN PATENT DOCUMENTS

CN    1198085 A    11/1998
CN    1699973 A    11/2005
(Continued)

OTHER PUBLICATIONS

Second Russian Action, including Search Report, for corresponding Russian Patent Application No. 2021120270, dated Apr. 4, 2022, 15 pages.
(Continued)

*Primary Examiner* — Eric F Winakur
(74) *Attorney, Agent, or Firm* — Westman, Champlin & Koehler, P.A.

(57) ABSTRACT

A non-invasive detection method, device, system and wearable apparatus for tissue element are provided. The method includes: emitting incident light of multiple predetermined wavelengths to a detected site, respectively; for each predetermined wavelength, obtaining light intensity values emitted from a surface of the detected site based on multiple photosensitive surfaces, wherein multiple photosensitive surfaces are at predetermined distances from a center of the incident light; and determining a concentration of the tissue element to be detected according to light intensity values in multiple predetermined wavelengths.

14 Claims, 12 Drawing Sheets

(56) References Cited

U.S. PATENT DOCUMENTS

| | | | |
|---|---|---|---|
| 8,552,359 | B2 | 10/2013 | Xu |
| 8,996,338 | B2 | 3/2015 | Xu et al. |
| 10,054,594 | B2 | 8/2018 | Xu et al. |
| 10,271,747 | B2 | 4/2019 | Ozawa et al. |
| 2005/0020892 | A1 | 1/2005 | Acosta et al. |
| 2007/0208231 | A1 | 9/2007 | Dipl-Ing |
| 2010/0252721 | A1 | 10/2010 | Xu |
| 2010/0331636 | A1 | 12/2010 | Hubner et al. |
| 2011/0131021 | A1 | 6/2011 | Xu et al. |
| 2013/0035568 | A1 | 2/2013 | Toriumi et al. |
| 2015/0342508 | A1 | 12/2015 | Chong |
| 2016/0091496 | A1 | 3/2016 | Xu et al. |
| 2016/0231235 | A1 | 8/2016 | Gulati et al. |
| 2016/0242682 | A1 | 8/2016 | Gulati et al. |
| 2016/0287894 | A1 | 10/2016 | Arai et al. |
| 2016/0313244 | A1 | 10/2016 | Shiono |
| 2017/0027511 | A1 | 2/2017 | Connor |
| 2017/0273576 | A1 | 9/2017 | Ozawa et al. |

FOREIGN PATENT DOCUMENTS

| | | |
|---|---|---|
| CN | 101288587 A | 10/2008 |
| CN | 101292875 A | 10/2008 |
| CN | 101686803 A | 3/2010 |
| CN | 103149177 A | 6/2013 |
| CN | 104287693 A | 1/2015 |
| CN | 204336925 U | 5/2015 |
| CN | 105510238 A | 4/2016 |
| CN | 105559794 A | 5/2016 |
| CN | 107233088 A | 10/2017 |
| CN | 108078549 | 5/2018 |
| CN | 108152214 A | 6/2018 |
| CN | 108261202 A | 7/2018 |
| CN | 108577860 A | 9/2018 |
| EP | 1169965 A1 | 1/2002 |
| EP | 3220824 A1 | 9/2017 |
| JP | 2003210465 A | 7/2003 |
| JP | 2004267613 A | 9/2004 |
| JP | 2004337605 A | 12/2004 |
| JP | 2005334281 A | 12/2005 |
| JP | 2006231075 A | 9/2006 |
| JP | 2007020735 A | 2/2007 |
| JP | 2007330550 A | 12/2007 |
| JP | 2013031502 A | 2/2013 |
| JP | WO2011081141 A1 | 5/2013 |
| JP | 2015089489 A | 5/2015 |
| JP | 2015225081 A | 12/2015 |
| JP | 2016206175 A | 12/2016 |
| JP | 2017051317 A | 3/2017 |
| JP | 2017223548 A | 12/2017 |
| JP | 2018021833 A | 2/2018 |
| RU | 2595488 C2 | 8/2016 |
| WO | 2016086448 A1 | 6/2016 |

OTHER PUBLICATIONS

First Japanese Action, including Search Report, for corresponding Japanese Patent Application No. 2021-533668, dated Apr. 4, 2022, 12 pages.
International Search Report (including English translation) and Written Opinion for International Application No. PCT/CN2019/125781, dated Mar. 13, 2020, 10 pages.
First Office Action, including Search Report, for Chinese Patent Application No. 201980079550.8, dated Jun. 20, 2022, 16 pages.
First Office Action, including Search Report, for Chinese Patent Application No. 201911296223.6, dated Jun. 17, 2022, 15 pages.
First Office Action, including Search Report, for Chinese Patent Application No. 201911296224.0, dated Jun. 20, 2022, 19 pages.
Second Examination Report, for corresponding Canadian Patent Application No. 3,122,875, dated Nov. 30, 2023, 3 pages.
Notice of Preliminary Rejection, for corresponding Korean Patent Application No. 10-2021-7021729, dated Oct. 31, 2023, 11 pages.
Third Office Action, including Search Report, for corresponding Russian Patent Application No. 2021120270, dated Aug. 19, 2022, 17 pages.
Extended European Search Report, for corresponding European Patent Application No. 19895324.2, dated Aug. 5, 2022, 7 pages.
First Examination Report, for corresponding Canadian Patent Application No. 3,122,875, dated Aug. 23, 2022, 4 pages.
First Examination Report, for corresponding New Zealand Patent Application No. 777612, dated Aug. 23, 2022, 4 pages.
First Office Action, including Search Report, for corresponding Indian Patent Application No. 202147030838, dated May 12, 2022, 8 pages.
First Office Action, including Search Report, for corresponding Australian Patent Application No. 2019399791, dated May 9, 2022, 3 pages.
First Russian Action, including Search Report, for Russian Patent Application No. 2021120270, dated Nov. 16, 2021, 21 pages.
Second Examination Report, for corresponding New Zealand Patent Application No. 777612, dated Feb. 21, 2023, 6 pages.
Search Report and Written Opinion, for corresponding Singapore Patent Application No. 11202106281Q, dated Jan. 26, 2023, 8 pages.

NON-INVASIVE DETECTION METHOD, DEVICE, SYSTEM AND WEARABLE APPARATUS FOR TISSUE ELEMENT

CROSS-REFERENCE TO RELATED APPLICATION

This application is a Section 371 National Stage Application of International Application No. PCT/CN2019/125781, filed on Dec. 16, 2019, entitled "NON-INVASIVE DETECTION METHOD, DEVICE, SYSTEM AND WEARABLE APPARATUS FOR TISSUE ELEMENT," which claims priority to Chinese Application No. 201811539082.1, filed on Dec. 14, 2018, incorporated herein by reference in their entirety.

TECHNICAL FIELD

The present disclosure relates to a field of spectrum detection technology, and in particular, to a non-invasive detection method, device, system and wearable apparatus for tissue element.

BACKGROUND

Body fluids of human body contain a variety of tissue elements, such as blood sugar, fat, and white blood cells, etc. A concentration of each tissue element must be within its corresponding concentration range to ensure a healthy operation of the human body. However, for some individuals, because the tissue element is prone to imbalance, that is, the concentration of the tissue element is not within the numerical range, it may cause the body to suffer from disease, harm health and even life. Therefore, for such individuals, the tissue element thereof needs to be detected in real time.

Since optical methods have characteristics of rapidness, non-invasiveness, and multidimensional information, etc., the prior art usually adopts the optical methods to detect the tissue element. According to measurement principles, the optical methods mainly include Raman spectroscopy, polarization method, optical coherence tomography, photoacoustic spectroscopy, mid-infrared spectroscopy, and near-infrared spectroscopy, etc.

However, it has been found that at least the following problems exist in the prior art. Firstly, the signal-to-noise ratio is low. Since the diffusely-scattered light emitted through the detected tissue itself is relatively weak, a change in the diffusely-scattered light caused by a change in the concentration of the tissue element to be detected is also weak, and a light receiving efficiency is low, so that the signal-to-noise of the received diffusely-scattered light signal is low, which directly affects a detection accuracy of the tissue element to be detected, resulting in a low detection accuracy. Secondly, a detection condition varies greatly. Because the detected tissue is soft tissue, every time the detection device is placed on the detected site for detection, and the detection conditions are different, so that a change in diffusely-scattered light caused by the detection condition is much greater than the change in the diffusely-scattered light caused by a change in the concentration of the tissue element to be detected, which causes the detection accuracy to be low. Wherein, the detection conditions may include an incident position of incident light, an incident angle of incident light, a contact pressure, and a temperature of the detected site, etc. Thirdly, the detected individual's own background noise is large. Water, fat, and protein in the blood of the detected individual are susceptible to physical and psychological background noises as the detected individual is a living body, so that it is difficult to extract weak signals under the interference of large background noises. The above problems result in the low detection accuracy.

SUMMARY

In the first aspect, the embodiments of the present disclosure provide a non-invasive detection method for tissue element, the method includes: an emitting step, wherein incident light of multiple predetermined wavelengths is respectively emitted to a detected site; an obtaining step, wherein for each predetermined wavelength, light intensity values emitted from a surface of the detected site are obtained based on multiple photosensitive surfaces, and the multiple photosensitive surfaces are located at predetermined distances from a center of the incident light; and a determination step, wherein a concentration of tissue element to be detected is determined according to the light intensity values in multiple predetermined wavelengths.

Optionally, the obtaining step includes: for each predetermined wavelength, at each predetermined distance, obtaining a light intensity value emitted from the surface of the detected site based on a photosensitive area including the photosensitive surfaces, wherein the photosensitive area is in one-to-one correspondence with the light intensity value.

Optionally, the obtaining step further includes: for each predetermined wavelength, obtaining the light intensity value emitted from the surface of the detected site based on M ring-shaped photosensitive surfaces, wherein multiple photosensitive surfaces are in one-to-one correspondence with the light intensity values, and $M \geq 1$.

Optionally, an inner diameter of each ring-shaped photosensitive surface is greater than or equal to 0.5 mm and less than or equal to 6 mm, and a ring width of each ring-shaped photosensitive surface is greater than or equal to 0.05 mm and less than or equal to 0.3 mm.

Optionally, when $M=4$, the inner diameters of M ring-shaped photosensitive surfaces from inside to outside in a radial direction are a first inner diameter, a second inner diameter, a third inner diameter and a fourth inner diameter, respectively; the first inner diameter is greater than or equal to 1.2 mm and less than 3 mm, the second inner diameter is greater than or equal to 3 mm and less than 3.8 mm, the third inner diameter is greater than or equal to 3.8 mm and less than 4.4 mm, and the fourth inner diameter is greater than or equal to 4.4 mm and less than 6 mm; alternatively, when $M=5$, the inner diameters of M ring-shaped photosensitive surfaces from inside to outside in the radial direction are a first inner diameter, a second inner diameter, a third inner diameter, a fourth inner diameter and a fifth inner diameter, respectively; the first inner diameter is greater than or equal to 1.2 mm and less than 2 mm, the second inner diameter is greater than or equal to 2 mm and less than 2.8 mm, the third inner diameter is greater than or equal to 2.8 mm and less than 3.6 mm, the fourth inner diameter is greater than or equal to 3.6 mm and less than 4.2 mm, and the fifth inner diameter is greater than or equal to 4.2 mm and less than 6 mm.

Optionally, the ring width of each ring-shaped photosensitive surface is 0.1 mm or 0.2 mm.

Optionally, each predetermined wavelength is greater than or equal to 900 nm and less than or equal to 2400 nm.

Optionally, the determination step includes: from the light intensity values in multiple predetermined wavelengths, determining one light intensity value as a light intensity target value in the multiple predetermined wavelengths; and determining the concentration of the tissue element to be detected according to the light intensity target value in the multiple predetermined wavelengths.

Optionally, the determination step includes: determining a light intensity measurement value and a light intensity reference value from the light intensity values in multiple predetermined wavelengths; and determining the concentration of the tissue element to be detected according to the light intensity measurement value and the light intensity reference value in the multiple predetermined wavelengths.

Optionally, the determining the light intensity measurement value and the light intensity reference value from the light intensity values in multiple predetermined wavelengths includes: for each predetermined wavelength, determining the light intensity measurement value and the light intensity reference value from the light intensity values corresponding to the predetermined wavelength according to predetermined conditions, wherein the predetermined conditions include at least one of a wavelength characteristic, an optical parameter and a skin structure parameter.

Optionally, for each predetermined wavelength, the determining the light intensity measurement value and the light intensity reference value from the light intensity values corresponding to the predetermined wavelength according to predetermined conditions includes: for each predetermined wavelength, according to a light intensity variation, determining the light intensity measurement value and the light intensity reference value from the light intensity values corresponding to the predetermined wavelength, wherein the light intensity measurement value is a light intensity value of which an absolute value of the light intensity variation is greater than or equal to a first variation threshold, the light intensity reference value is a light intensity value of which an absolute value of the light intensity variation is smaller than or equal to a second variation threshold, the light intensity variation is a variation between the light intensity value and corresponding predetermined light intensity value, the first variation threshold is greater than the second variation threshold, and the predetermined light intensity value is the light intensity value emitted from the surface of the detected site when the concentration of the tissue element to be detected is a predetermined concentration.

Optionally, the determining the concentration of the tissue element to be detected according to the light intensity measurement value and the light intensity reference value in the multiple predetermined wavelengths includes: for each predetermined wavelength, performing a differential operation on the light intensity measurement value and the light intensity reference value corresponding to the predetermined wavelength to obtain a differential light intensity value; and determining the concentration of the tissue element to be detected according to differential light intensity values in the multiple predetermined wavelengths.

Optionally, before the obtaining step, the method further includes: shielding interference light.

In a second aspect, embodiments of the present disclosure provide a non-invasive detection device for tissue element, including: a light source module, a detection module and a processing module; the detection module is in communication with the processing module; wherein the light source module is configured for respectively emitting incident light of multiple predetermined wavelengths to a detected site; the detection module is configured to obtain, for each predetermined wavelength, light intensity values emitted from a surface of the detected site based on multiple photosensitive surfaces, and to send the light intensity values to the processing module, wherein the multiple photosensitive surfaces are located at predetermined distances from a center of the incident light, and there are at least one predetermined distances; and the processing module is configured for determining the concentration of the tissue element to be detected according to the light intensity values in the multiple predetermined wavelengths.

Optionally, the detection module includes at least one photosensitive surface; anodes of different photosensitive surfaces in a same predetermined distance are electrically connected with each other; for each predetermined distance, at least one photosensitive surface is provided; the detection module is configured to obtain, under each predetermined distance, the light intensity value emitted from the surface of the detected site based on a photosensitive area including the photosensitive surfaces, wherein the photosensitive area is in one-to-one correspondence with the light intensity value.

Optionally, each of the multiple photosensitive surfaces is a ring-shaped photosensitive surface, different ring-shaped photosensitive surfaces are provided with a same geometric center, and M ring-shaped photosensitive surfaces are provided, wherein M≥1.

Optionally, an inner diameter of each ring-shaped photosensitive surface is greater than or equal to 0.5 mm and less than or equal to 6 mm, and a ring width of each ring-shaped photosensitive surface is greater than or equal to 0.05 mm and less than or equal to 0.3 mm.

Optionally, when M=4, the inner diameters of M ring-shaped photosensitive surfaces from inside to outside in a radial direction are a first inner diameter, a second inner diameter, a third inner diameter and a fourth inner diameter, respectively; the first inner diameter is greater than or equal to 1.2 mm and less than 3 mm, the second inner diameter is greater than or equal to 3 mm and less than 3.8 mm, the third inner diameter is greater than or equal to 3.8 mm and less than 4.4 mm, and the fourth inner diameter is greater than or equal to 4.4 mm and less than 6 mm; alternatively, when M=5, the inner diameters of M ring-shaped photosensitive surfaces from inside to outside in the radial direction are a first inner diameter, a second inner diameter, a third inner diameter, a fourth inner diameter and a fifth inner diameter, respectively; the first inner diameter is greater than or equal to 1.2 mm and less than 2 mm, the second inner diameter is greater than or equal to 2 mm and less than 2.8 mm, the third inner diameter is greater than or equal to 2.8 mm and less than 3.6 mm, the fourth inner diameter is greater than or equal to 3.6 mm and less than 4.2 mm, and the fifth inner diameter is greater than or equal to 4.2 mm and less than 6 mm.

Optionally, a ring width of each ring-shaped photosensitive surface is 0.1 mm or 0.2 mm.

Optionally, a range of each predetermined wavelength is greater than or equal to 900 nm and less than or equal to 2400 nm.

Optionally, the device further includes a first sleeve; the first sleeve is provided on an upper surface of the detection module, and an inner diameter of the first sleeve is greater than a diameter of an aperture on the detection module; and the first sleeve is configured for preventing surface reflected light that is generated by incident light passing through the surface of the detected site from entering the detection module, and, preventing diffracted light that is generated by incident light passing through the aperture of the detection module from entering the detection module.

Optionally, the detection module is further provided with a second sleeve connected integrally; the second sleeve is provided on an upper surface of the detection module, and an inner diameter of the second sleeve is greater than a diameter of an aperture on the detection module; and the second sleeve is configured for preventing surface reflected light that is generated by incident light passing through the surface of the detected site from entering the detection module, and preventing diffracted light that is generated by incident light passing through the aperture of the detection module from entering the detection module.

Optionally, the device further includes a third sleeve, an upper surface of the third sleeve passes through an aperture of the detection module, and exceeds an upper surface of the detection module; and the third sleeve is configured for preventing surface reflected light that side generated by incident light passing through the surface of the detected site from entering the detection module, and preventing diffracted light that is generated by incident light passing through the aperture of the detection module from entering the detection module.

Optionally, the device further includes a housing; wherein the light source module, the detection module and the processing module are provided inside the housing, and an upper surface of the detection module is lower than an upper surface of the housing.

Optionally, the device further includes a protection member; wherein the protection member is provided at an aperture of the upper surface of the housing, and an upper surface of the protection member is lower than the upper surface of the housing, the protection member is provided with an aperture, and has a same geometric center with the housing; a light transmittance of the protection member is greater than or equal to a light transmittance threshold; the protection member is configured for protecting the detection module, and, when the non-invasive detection device for tissue element is worn to the detected site, ensuring that a skin condition of the detected site remains in a natural state and realizing a non-contact detection.

Optionally, the device further includes a contact member; wherein the contact member is provided on the upper surface of the housing, and a thermal conductivity of material of the contact member is within a range of air thermal conductivity; the contact member is configured for ensuring that a skin condition of the detected site is remained in a natural state and realizing a non-contact detection when the non-invasive detection device for tissue element is worn to the detected site, and shortening a time for a thermal conduction between the non-invasive detection device when it is worn to the detected site and the detected site to reach a thermal equilibrium state by setting the thermal conductivity of the material of the contact member within the range of air thermal conductivity.

Optionally, the upper surface of the housing is plated with a heat-insulating material, and the thermal conductivity of the heat-insulating material is within the range of air thermal conductivity; the heat-insulating material is configured for ensuring that the skin condition of the detected site is remained in the natural state and realizing a non-contact detection when the non-invasive detection device for tissue element is worn to the detected site, and shortening a time for a thermal conduction between the non-invasive detection device when it is worn to the detected site and the detected site to reach a thermal equilibrium state by setting the thermal conductivity of the heat-insulating material within the range of air thermal conductivity.

Optionally, the light source module further includes a light source emitting unit or an incident optical fiber.

In third aspect, embodiments of the present disclosure provide a wearable apparatus, including: a body and the non-invasive detection device for tissue element as described above; wherein the non-invasive detection device for tissue element is provided on the body; and the wearable apparatus is worn to a detected site.

In fourth aspect, embodiments of the present disclosure provide non-invasive detection system for tissue element, including: the wearable apparatus as described above and a terminal; wherein the processing module is in communication with the detection module and the terminal, respectively; the wearable apparatus is worn to the detected site; the detection module is configured to obtain, for each predetermined wavelength, light intensity values emitted from a surface of the detected site based on multiple photosensitive surfaces, and to send the light intensity values to the processing module, wherein the multiple photosensitive surfaces are located at predetermined distances from a center of the incident light; the processing module is configured for processing the light intensity values in multiple predetermined wavelengths, obtaining processed light intensity values in multiple predetermined wavelengths, and send the processed light intensity values in multiple predetermined wavelengths to the terminal; and the terminal is configured for determining the concentration of the tissue element to be detected according to the processed light intensity values in multiple predetermined wavelengths.

DETAILED DESCRIPTION OF EMBODIMENTS

Figure 1:
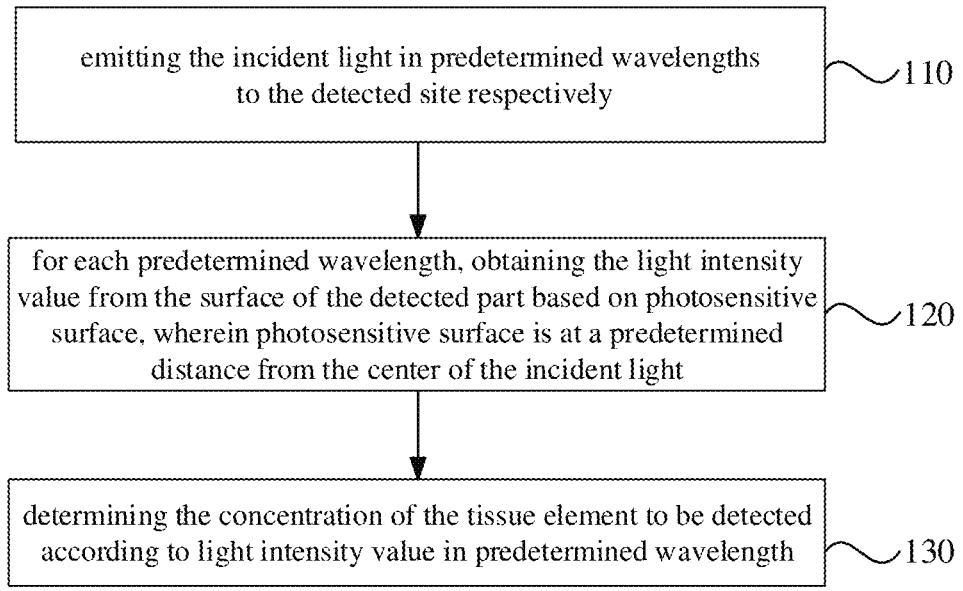
FIG. 1 is a flow chart of a non-invasive detection method for tissue element according to embodiments of the present disclosure.

The present disclosure will be further described in detail below with reference to the drawings and embodiments. It should be understood that the specific embodiments described here are only used to explain the present disclosure, rather than limiting the present disclosure. Various features described in the embodiments may be combined to form multiple alternative solutions. In addition, it should be noted that, for ease of description, only parts related to the present disclosure, rather than all of the structures are shown in the drawings.

To improve a detection accuracy, modifications may be made from three aspects: firstly, improve a light receiving efficiency; secondly, stabilize a detection condition; thirdly, eliminate common mode interference information. Wherein, the first aspect may be realized by improving an efficiency of receiving homogeneous scattered light to a maximum extent. The homogeneous scattered light is diffusely-scattered light with a substantially same transmitting path. The second aspect may be realized by a small size and a light weight of the non-invasive detection device for tissue element. And the third aspect may be realized by using a differential processing in conjunction with floating reference theory. To better understand the technical solutions provided by the embodiments of the present disclosure, some concepts involved will be described in the following firstly.

For a human body, body tissues may be simplified into a complex medium constituted by a scattering body and a scattering background, when incident light enters the tissue, absorption and scattering will occur, the absorption will directly cause an attenuation of light energy, and the scattering will affect a light energy distribution by changing a transmitting direction of photon, a light intensity distribution of diffusely-scattered light emitted from a detected site is a result of a combined effect of the absorption and the scattering. Based on floating reference theory, for the tissue element to be detected, there is a certain area at which the absorption and the scattering have a same influence on the diffusely-scattered light intensity and opposite directions, therefore the diffusely-scattered light intensity is not sensitive to a change in a concentration of the tissue element to be detected. A position with above characteristics may be referred to as a reference position (or a benchmark position). The diffusely-scattered light intensity at the reference position reflects a response of other interferences other than the tissue element to be detected during a detection process. Moreover, for the tissue element to be detected, there may also be a certain position at which a sensitivity of the diffusely-scattered light intensity to the change of the concentration of the tissue element to be detected is greater than or equal to a sensitivity threshold. The position with the above characteristics may be referred to as a measurement position. The diffusely-scattered light intensity at the measurement position reflects the response of the tissue element to be detected, and, the response of other interferences other than the tissue element to be detected. In addition, the above response reflecting the tissue element to be detected may be referred to as effective information. In the following, the above content will be described with reference to the specific embodiments.

FIG. 1 is a flow chart of a non-invasive detection method for tissue element provided by the embodiments of the present disclosure, and the embodiments may be applied for providing a condition of a detection accuracy of the concentration of the tissue element to be detected. The embodiments of the present disclosure may provide the non-invasive detection device for tissue element, the non-invasive detection device for tissue element may be realized by manners such as software and/or hardware, the non-invasive detection device for tissue element may be configured in a wearable apparatus, such as a smart watch. As shown in FIG. 1, specifically, the method includes the following steps.

In step 110, incident light of multiple predetermined wavelengths is emitted to the detected site, respectively.

In the embodiments of the present disclosure, incident light of multiple predetermined wavelengths may be emitted to the detected site through a light source module. The detected site may include parts such as palms, arms and earlobes, etc. Each predetermined wavelength may be greater than or equal to 900 nm and less than or equal to 2400 nm. There may be at least one predetermined wavelength. The incident light may be collimated light, or may be non-collimated light.

In step 120, for each predetermined wavelength, the light intensity values emitted from the surface of the detected site are obtained based on multiple photosensitive surfaces, and multiple photosensitive surfaces are located at corresponding predetermined distances from a center of the incident light.

In the embodiments of the present disclosure, the photosensitive surface may be configured for obtaining the light intensity value emitted from the surface of the detected site. A distance of the photosensitive surface to the center of the incident light may be referred to as the predetermined distance. In this case, the predetermined distance may be understood as a source-detection distance, that is, the distance from the photosensitive surface to the incident light. Predetermined distances corresponding to different photosensitive surfaces may be the same, or may be different. Directions corresponding to different photosensitive surfaces may be the same, or may be different. The position and the number of the predetermined distances may be adjusted according to actual conditions, which will not be defined specifically herein. At least one photosensitive surface may be corresponded to the same one predetermined distance, the number of the photosensitive surfaces corresponding to different predetermined distances may be the same, or may be different, it may be adjusted according to actual conditions, and will not be defined specifically herein. Each photosensitive surface corresponding to different predetermined wavelengths is the same.

For each predetermined wavelength, under each predetermined distance, the light intensity value emitted from the surface of the detected site is obtained based on a photosensitive area including the photosensitive surfaces, the photosensitive area is in one-to-one correspondence with the light intensity value, and the number of the predetermined distance is at least one. Based on this, the light intensity value corresponding to each predetermined wavelength may be obtained.

In step 130, the concentration of the tissue element to be detected is determined according to light intensity values in multiple predetermined wavelengths.

In the embodiments of the present disclosure, after obtaining the light intensity values of multiple predetermined wavelengths, the concentration of the tissue element to be detected may be determined according to light intensity values in multiple predetermined wavelengths. According to the number of the light intensity values, there may be different manners. In the first manner, the number of the light intensity values in multiple predetermined wavelengths is one, multiple photosensitive surfaces correspond to the same one predetermined distance. In this case, the concentration of the tissue element to be detected may be directly determined according to original light intensity value in multiple predetermined wavelengths. Specifically, the light intensity values in multiple predetermined wavelengths may be input into a prediction model for tissue element generated by pre-training to obtain a prediction result, which is the concentration of the tissue element to be detected. In the second manner, the number of the light intensity values of multiple predetermined wavelengths is at least two, multiple photosensitive surfaces correspond to different predetermined distances. In this case, differential operation may be taken to determine the concentration of the tissue element to be detected. That is, for each predetermined wavelength, two light intensity values may be determined from light intensity values under the predetermined wavelength, and the two light intensity values are subjected to a differential operation to determine the differential light intensity value under the predetermined wavelength. And the concentration of the tissue element to be detected is determined according to the differential light intensity values under the predetermined wavelength. Specifically, the differential light intensity values of multiple predetermined wavelengths may be input into a prediction model for tissue element generated by pre-training to obtain a prediction result, which is the concentration of the tissue element to be detected. The specific calculation process may refer to patent document with a publication number CN1699973A, which will not be detailed herein.

After the incident light is transmitted to the surface of the detected site, a part of the incident light will enter the inside of the detected site, and it interacts with the tissue to be absorbed and scattered during the transmission process, and then it is emitted in a form of diffusely scattered light from the surface of the detected site. Due to the different transmission paths of light in the tissue, the diffusely-scattered light will emit from the surface of the detected site at different distances from the center of the incident light, and carry different effective information, but the common mode interference information carried is basically the same, the effective information is the response of the tissue element to be detected during the detection process. Since the diffusely-scattered light emitted from the surface of the detected site at different distances from the center of the incident light carries different effective information, but the common mode interference information carried is substantially the same, the concentration of the tissue element to be detected may be determined according to the two original light intensity values, in order to improve the detection accuracy and eliminate the influence of the common mode interference information. The predetermined distances corresponding to the two original light intensity values are different. It should be understood that, at least two predetermined distances need to be provided, so that the concentration of the tissue element to be detected may be determined according to the light intensity values at the two predetermined distances. Therefore, the above-mentioned differential operation may eliminate the influence of common mode interference information on the detection result and improve the detection accuracy.

The technical solution of the embodiment obtains the light intensity values emitted from the surface of the detected site based on multiple photosensitive surfaces for each predetermined wavelength, and determines the concentration of the tissue element to be detected according to the light intensity values of multiple predetermined wavelengths. As a wide range of light intensity values may be received, the light receiving efficiency is improved, and the detection accuracy of the tissue element to be detected is improved. Moreover, due to different light intensity values may be differentially operated, the common mode interference information may be eliminated, and therefore, the detection accuracy of the tissue element to be detected is also improved.

Optionally, on the basis of the above-mentioned technical solution, the step 120 may include: for each predetermined wavelength, under each predetermined distance, obtaining the light intensity value emitted from the surface of the detected site based on the photosensitive area including photosensitive surfaces, and the photosensitive area is in one-to-one correspondence with the light intensity value.

In the embodiments of the present disclosure, due to the low light receiving efficiency, a signal-to-noise ratio of the signal is low so that the detection accuracy cannot meet the clinical accuracy requirements. Therefore, in order to further improve the detection accuracy, it is possible to improve the light receiving efficiency. In order to improve the light receiving efficiency, an arrangement of the photosensitive surface needs to be designed accordingly. According to a design idea, after the incident light is transmitted to the surface of the detected site, a part of the incident light will enter the inside of the detected site, it interacts with the tissue to be absorbed and scattered during the transmission process, and then emits in the form of diffusely-scattered light from the surface of the detected site. Due to the different transmission paths of light in the tissue, the diffusely-scattered light will emit from the surface of the detected site at different distances from the center of the incident light, and carry different effective information. However, the carried common mode interference information is substantially the same, and the effective information is the response of the tissue element to be detected during the detection process. Since homogeneous scattered light has substantially the same transmission path, the information carried by the homogeneous scattered light is substantially the same. If the receiving efficiency of the homogeneous scattered light may be improved, the light receiving efficiency may be improved. That is, by improving the receiving efficiency of the homogeneous scattered light, the light receiving efficiency may be improved.

Figure 2:
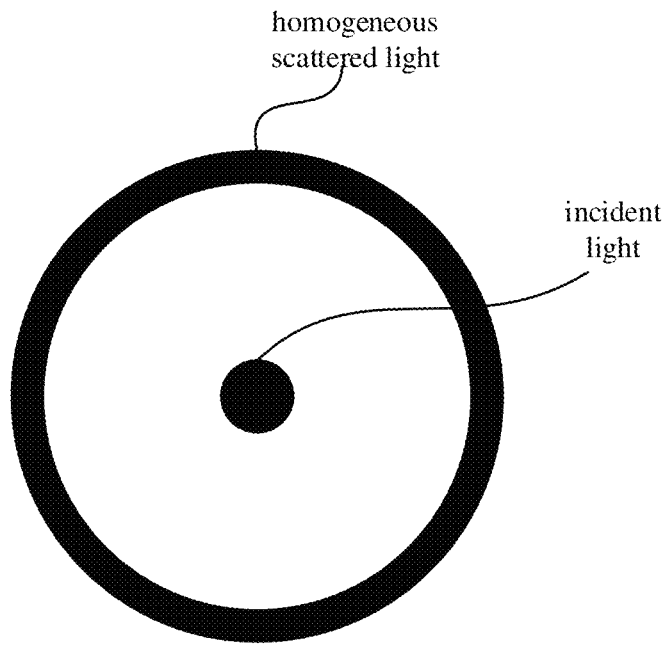
FIG. 2 is a schematic diagram of an emission area of homogeneous scattered light according to the embodiments of the present disclosure.

Since the homogeneous scattered light has substantially the same transmission path, the emission position of the homogeneous scattered light on the surface of the detected site will form a ring with the center of the incident light as an origin, and a distance between the emission position and the center of the incident light as a radius, that is, the emission area of the homogeneous scattered light is ring-shaped. Details of which may refer to FIG. 2, as shown in FIG. 2, a schematic diagram of the emission area of the homogeneous scattered light is shown. Based on the above, if the light intensity value emitted from the above-mentioned emission area may be obtained as much as possible, the receiving efficiency of the homogeneous scattered light may be improved, and then the light receiving efficiency may be improved, thereby the detection accuracy is improved. It should be understood that the distances between the emission position of the homogeneous scattered light and the center of the incident light are basically the same, but the directions are different. Based on this, for each predetermined wavelength, the predetermined distance and the photosensitive surface may be predetermined.

In order to improve the receiving efficiency of the homogeneous scattered light as much as possible, for each predetermined wavelength, under each predetermined distance, at least one photosensitive surface may be provided, and all the photosensitive surfaces may form a photosensitive area. Based on the photosensitive area, a photoelectric conversion is realized, and therefore the light intensity value emitted from the surface of the detected site is obtained, that is, a light intensity value including the light emitted from the surface of the detected site by at least one photosensitive surface. The photosensitive area is in one-to-one correspondence with the light intensity value, that is, each photosensitive area corresponds to one light intensity value. Based on this, each light intensity value corresponding to each predetermined distance under the predetermined wavelength may be obtained, and the number of the predetermined distances may be at least one. That is, for each predetermined wavelength, at T photosensitive surfaces with the same predetermined distance, a light intensity value of the light emitted by the surfaces of the T detected sites is obtained, where T≥1, and the number of the photosensitive surfaces corresponding to different predetermined distances may be the same or different. The number of the predetermined distances is at least one.

Figure 3:
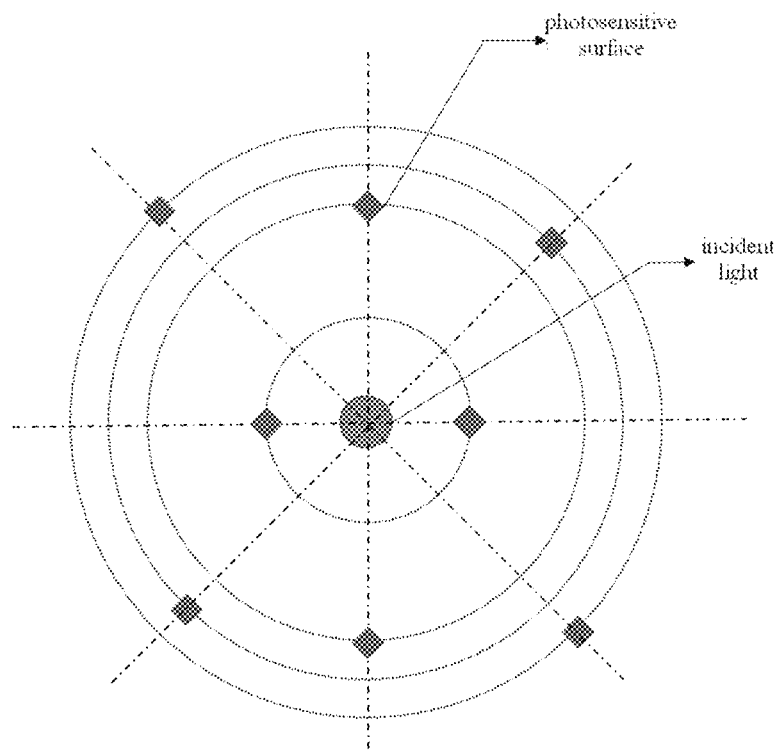
FIG. 3 is a schematic diagram of an arrangement of photosensitive surfaces according to the embodiments of the present disclosure.
Figure 4:
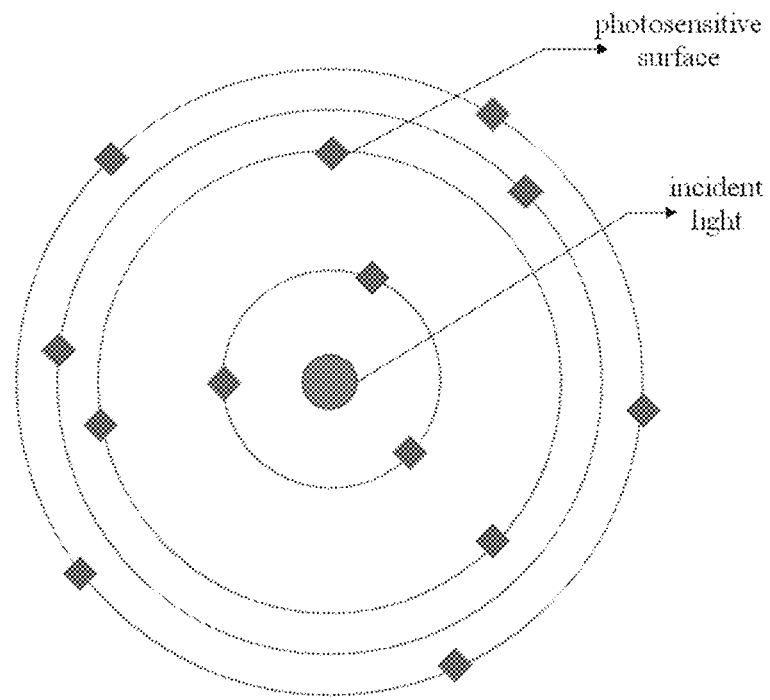
FIG. 4 is a schematic diagram of another arrangement of photosensitive surfaces according to the embodiments of the present disclosure.

It should be noted that, for each predetermined distance, the number of the corresponding photosensitive surfaces may be provided according to actual conditions, which is not limited here. The number of the photosensitive surfaces corresponding to the different predetermined distances may be the same or different, and may be provided according to actual conditions, which is not limited here. As shown in FIG. 3 and FIG. 4, FIG. 3 shows a schematic diagram of a distribution of photosensitive surfaces. FIG. 4 shows another distribution diagram of photosensitive surfaces. In FIG. 3, the number of the photosensitive surfaces corresponding to the different predetermined distances is the same. FIG. 4 shows that the number of the photosensitive surfaces corresponding to the different predetermined distances is different.

It should also be noted that, for each predetermined distance, the corresponding photosensitive area may include at least one photosensitive surface. The photosensitive surface may be a discrete circular surface or a polygonal surface, or may be a discrete fan ring, or a complete ring surface. Among them, an area of the discrete circular and an area of the polygonal surface should not be too large. Referring to FIG. 3 and FIG. 4 for details, the photosensitive surface in FIG. 3 and FIG. 4 is a discrete square surface.

It should also be noted that for each predetermined distance, the photosensitive surface distribution may form a symmetrical distribution centered on the center of the incident light, or an asymmetrical distribution centered on the center of the incident light. The above may be provided according to actual conditions, which is not limited here. As shown in FIG. 3 and FIG. 4, FIG. 3 shows a symmetrical distribution. FIG. 4 shows an asymmetric distribution.

Figure 5:
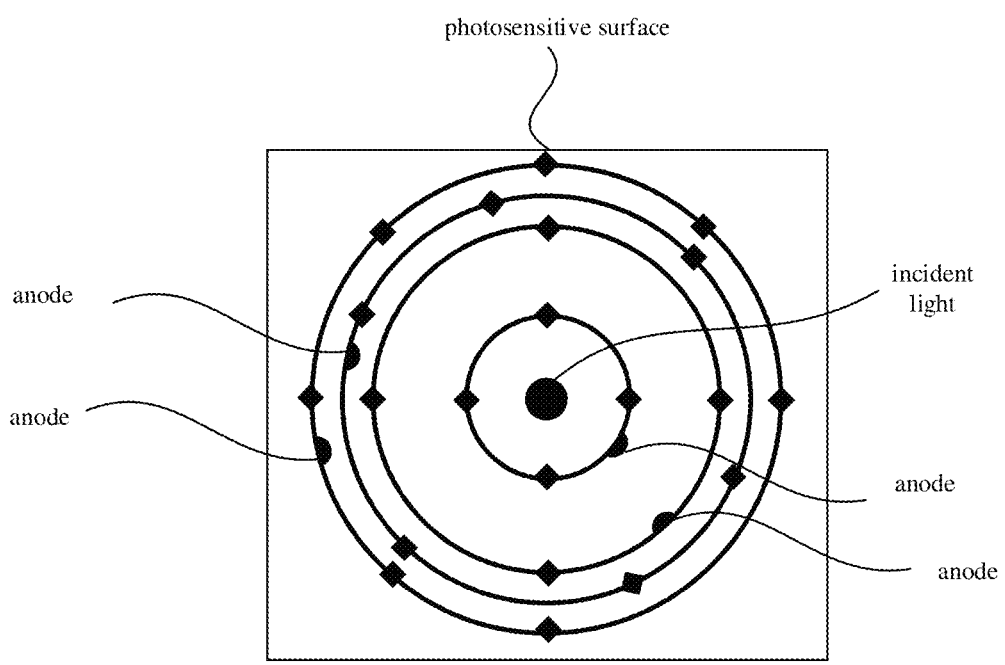
FIG. 5 is a schematic diagram of an electrical connection of anodes in a photosensitive area according to the embodiments of the present disclosure.

It should also be noted that the light intensity value corresponding to each photosensitive area may be realized by connecting the anodes of the photosensitive surfaces to output signals. Referring to FIG. 5 for details. FIG. 5 shows a schematic diagram of an electrical connection of anodes in the photosensitive area.

It should also be noted that if there is one predetermined distance, in the above case, the differential operation may not be configured to process the light intensity value to determine the concentration of the tissue element to be detected. However, because the above detection method itself has greatly improved the light receiving efficiency and improved the signal-to-noise ratio of the signal, even if the differential operation is not used, the detection accuracy is also improved due to the improvement of the signal-to-noise ratio. If there are at least two predetermined distances, in the above case, after light intensity values is obtained, differential operation may be configured to determine the concentration of the tissue element to be detected. Compared with one predetermined distance, since the differential operation may eliminate the common mode interference information, the detection accuracy may be further improved. Of course, if there are two predetermined distances, the differential operation may not be used.

In the above-mentioned detection by using the photosensitive area, each photosensitive area is including photosensitive surfaces with the same predetermined distance to obtain the light intensity value emitted from the surface of the detected site, which may improve the receiving efficiency of the homogeneous scattered light.

Optionally, on the basis of the above technical solution, for each predetermined wavelength and under each predetermined distance, the light intensity value emitted from the surface of the detected site is obtained based on the photosensitive area including the photosensitive surfaces, and the photosensitive area is in one-to-one correspondence with the light intensity value. Specifically, for each predetermined wavelength, detection is performed based on M ring-shaped photosensitive surfaces to obtain the light intensity value emitted from the surface of the detected site, each ring-shaped photosensitive surface is in one-to-one correspondence with the light intensity value, where M≥1.

In the embodiments of the present disclosure, it may be seen from the above that the emission area including the homogeneous scattered light is a ring-shaped area. Therefore, in order to improve the receiving efficiency of the homogeneous scattered light, detection may be performed through the ring-shaped photosensitive surface. Each ring-shaped photosensitive surface may obtain the light intensity value emitted from the corresponding area. Each ring-shaped photosensitive surface may correspond to a source-detection distance. Since the ring-shaped photosensitive surface may receive the light intensity value of the homogeneous scattered light in a range of 360°, it may receive the homogeneous scattered light to the greatest extent, thereby improving the receiving efficiency of the homogeneous scattered light. As the receiving efficiency of homogeneous scattered light is improved, the detection accuracy is also improved. As stated above, for each predetermined wavelength, detection is performed based on M ring-shaped photosensitive surfaces to obtain the light intensity value emitted from the surface of the detected site, and each ring-shaped photosensitive surface is in one-to-one correspondence with the light intensity value, where M≥1. In other words, for each predetermined wavelength, based on the ring-shaped photosensitive area including T photosensitive surfaces, the light intensity value emitted from the surface of the detected site is obtained, and each ring-shaped photosensitive area corresponds to one light intensity Value, where T≥1.

It should be noted that the number of ring-shaped photosensitive surfaces and the size of the ring-shaped photosensitive surfaces may be provided according to actual conditions, which are not specifically limited here. The provision according to actual conditions mentioned here may be understood as provided according to wavelength characteristics, optical parameters and skin structure parameters. This is because the above will affect the transmission path of the incident light in the tissue.

It should also be noted that if M=1, that is, the light intensity value emitted from the surface of the detected site is obtained through the detection of one ring-shaped photosensitive surface, in the above case, the differential operation may not be configured to process the light intensity value to determine the concentration of the tissue element to be detected. However, since the ring-shaped detection itself has greatly improved the light receiving efficiency, thereby increasing the signal-to-noise ratio of the signal, even if the differential operation is not used, the detection accuracy is still improved due to the improvement of the signal-to-noise ratio. If M≥2, that is, the light intensity value emitted from the surface of the detected site is obtained through the detection of at least two ring-shaped photosensitive surfaces, in the above case, after light intensity values are obtained, the differential operation may be configured to determine the concentration of the tissue element to be detected. Compared with M=1, since the differential operation may eliminate the common mode interference information, the detection accuracy may be further improved. Of course, if M≥2, the differential operation may not be used.

Optionally, on the basis of the above technical solution, an inner diameter of each ring-shaped photosensitive surface may be greater than or equal to 0.5 mm or less than or equal to 6 mm, and a ring width of each ring-shaped photosensitive surface may be greater than or equal to 0.05 mm or less than or equal to 0.3 mm.

In the embodiments of the present disclosure, the inner diameter refers to the diameter. The M ring-shaped photosensitive surfaces may be arranged in the same geometric center, and the inner diameters of different ring-shaped photosensitive surfaces have different distances from the center. The ring widths of different ring-shaped photosensitive surfaces may be the same or different, and may be provided according to actual situations, which is not limited here. A range of the inner diameter and a range of the ring width of each ring-shaped photosensitive surface may be determined by experimental results obtained from experiments conducted on different predetermined wavelengths and different detected individuals. In a radial direction, the inner diameters of the M ring-shaped photosensitive surfaces from inside to outside may be referred to as the first inner diameter, the second inner diameter, . . . , the $(M-1)^{th}$ inner diameter, and the $M^{th}$ inner diameter, respectively. The range of the predetermined wavelength may be greater than or equal to 900 nm and less than or equal to 2400 nm.

Optionally, if M=1, then if the first inner diameter is 0.5 mm, the ring width of the ring-shaped photosensitive surface is 0.05 mm, and the predetermined wavelength is 900 nm, then in this case, the light intensity value emitted from the surface of the detected site through the detection of the ring-shaped photosensitive surface is 0.136V. If the first inner diameter is 3 mm, the ring width of the ring-shaped photosensitive surface is 0.05 mm, and the predetermined wavelength is 900 nm, then in this case, the light intensity value emitted from the surface of the detected site through the detection of the ring-shaped photosensitive surface is 0.654V. If the first inner diameter is 1.5 mm, the ring width of the ring-shaped photosensitive surface is 0.05 mm, and the predetermined wavelength is 900 nm, then in this case, the light intensity value emitted from the surface of the detected site through the detection of the ring-shaped photosensitive surface is 0.401V. If the first inner diameter is 0.5 mm, the ring width of the ring-shaped photosensitive surface is 0.3 mm, and the predetermined wavelength is 900 nm, then in this case, the light intensity value emitted from the surface of the detected site through the detection of the ring-shaped photosensitive surface is 1.168V. If the first inner diameter is 0.5 mm, the ring width of the ring-shaped photosensitive surface is 0.2 mm, and the predetermined wavelength is 900 nm, then in this case, the light intensity value emitted from the surface of the detected site through the detection of the ring-shaped photosensitive surface is 0.702V. If the first inner diameter is 3 mm, the ring width of the ring-shaped photosensitive surface is 0.05 mm, and the predetermined wavelength is 2400 nm, then in this case, the light intensity value emitted from the surface of the detected site through the detection of the ring-shaped photosensitive surface is 2.678V. If the first inner diameter is 3 mm, the ring width of the ring-shaped photosensitive surface is 0.05 mm, and the predetermined wavelength is 1400 nm, then in this case, the light intensity value emitted from the surface of the detected site through the detection of the ring-shaped photosensitive surface is 0.571V.

Optionally, if M=4, the first inner diameter may be greater than or equal to 1.2 mm and less than 3 mm, the second inner diameter may be greater than or equal to 3 mm and less than 3.8 mm, the third inner diameter may be greater than or equal to 3.8 mm and less than 4.4 mm, the fourth inner diameter may be greater than or equal to 4.4 mm and less than 6 mm, then if the first inner diameter is 1.2 mm, the second inner diameter is 3 mm, the third inner diameter is 3.8 mm, the fourth inner diameter is 4.4 mm, the predetermined wavelength is 900 nm, and the ring width of each ring-shaped photosensitive surface is 0.05 mm, then in this case, the light intensity values emitted from the surface of the detected site through the detection of the ring-shaped photosensitive surface are 0.316V, 0.632V, 0.611V and 0.508V, respectively.

If the first inner diameter is 2 mm, the second inner diameter is 3 mm, the third inner diameter is 3.8 mm, the fourth inner diameter is 4.4 mm, the predetermined wavelength is 900 nm, and the ring width of each ring-shaped photosensitive surface is 0.05 mm, then in this case, the light intensity values emitted from the surface of the detected site through the detection of the ring-shaped photosensitive surface are 0.496V, 0.632V, 0.611V and 0.508V, respectively.

If the first inner diameter is 2 mm, the second inner diameter is 3.6 mm, the third inner diameter is 3.8 mm, the fourth inner diameter is 4.4 mm, the predetermined wavelength is 900 nm, and the ring width of each ring-shaped photosensitive surface is 0.05 mm, then in this case, the light intensity values emitted from the surface of the detected site through the detection of the ring-shaped photosensitive surface are 0.496V, 0.639V, 0.611V and 0.508V, respectively.

If the first inner diameter is 2 mm, the second inner diameter is 3.6 mm, the third inner diameter is 4 mm, the fourth inner diameter is 4.4 mm, the predetermined wavelength is 900 nm, and the ring width of each ring-shaped photosensitive surface is 0.05 mm, then in this case, the light intensity values emitted from the surface of the detected site through the detection of the ring-shaped photosensitive surface are 0.496V, 0.639V, 0.596V and 0.508V, respectively.

If the first inner diameter is 2 mm, the second inner diameter is 3.6 mm, the third inner diameter is 3.8 mm, the fourth inner diameter is 6 mm, the predetermined wavelength is 900 nm, and the ring width of each ring-shaped photosensitive surface is 0.05 mm, then in this case, the light intensity values emitted from the surface of the detected site through the detection of the ring-shaped photosensitive surface are 0.496V, 0.639V, 0.611V and 0.265V, respectively.

If the first inner diameter is 2 mm, the second inner diameter is 3.6 mm, the third inner diameter is 3.8 mm, the fourth inner diameter is 5 mm, the predetermined wavelength is 900 nm, and the ring width of each ring-shaped photosensitive surface is 0.05 mm, then in this case, the light intensity values emitted from the surface of the detected site through the detection of the ring-shaped photosensitive surface are 0.496V, 0.639V, 0.611V and 0.312V, respectively.

If the first inner diameter is 2 mm, the second inner diameter is 3.6 mm, the third inner diameter is 3.8 mm, the fourth inner diameter is 4.4 mm, the predetermined wavelength is 2400 nm, and the ring width of each ring-shaped photosensitive surface is 0.05 mm, then in this case, the light intensity values emitted from the surface of the detected site through the detection of the ring-shaped photosensitive surface are 2.085V, 2.006V, 2.331V and 1.518V, respectively.

If the first inner diameter is 2 mm, the second inner diameter is 3.6 mm, the third inner diameter is 3.8 mm, the fourth inner diameter is 4.4 mm, the predetermined wavelength is 1400 nm, and the ring width of each ring-shaped photosensitive surface is 0.05 mm, then in this case, the light intensity values emitted from the surface of the detected site through the detection of the ring-shaped photosensitive surface are 0.449V, 0.574V, 0.561V and 0.467V, respectively.

If the first inner diameter is 2 mm, the second inner diameter is 3.6 mm, the third inner diameter is 3.8 mm, the fourth inner diameter is 5 mm, the predetermined wavelength is 1400 nm, and the ring width of each ring-shaped photosensitive surface is 0.3 mm, then in this case, the light intensity values emitted from the surface of the detected site through the detection of the ring-shaped photosensitive surface are 2.941V, 3.335V, 3.189V and 2.415V, respectively.

If the first inner diameter is 2 mm, the second inner diameter is 3.6 mm, the third inner diameter is 3.8 mm, the fourth inner diameter is 4.4 mm, the predetermined wavelength is 900 nm, and the ring width of each ring-shaped photosensitive surface is 0.2 mm, then in this case, the light intensity values emitted from the surface of the detected site through the detection of the ring-shaped photosensitive surface are 2.012V, 2.325V, 2.301V and 0.168V, respectively.

It should be noted that, those skilled in the art may continue the same idea as described above to provide other numbers of ring-shaped photosensitive surfaces, and, provide the size of each ring-shaped photosensitive surface, which will not be repeated here. Furthermore, the ring-shaped photosensitive surface used may be selected according to actual conditions, that is, although M ring-shaped photosensitive surfaces are provided, however, the light intensity values obtained from only H ring-shaped photosensitive surfaces therein may be used actually to participate in determining the concentration of the tissue element to be detected, wherein $0<H \leq M$.

Optionally, on the basis of the above technical solution, if $M=4$, the first inner diameter may be greater than or equal to 1.2 mm and less than 3 mm, the second inner diameter may be greater than or equal to 3 mm and less than 3.8 mm, the third inner diameter may be greater than or equal to 3.8 mm and less than 4.4 mm, the fourth inner diameter may be greater than or equal to 4.4 mm and less than 6 mm. Alternatively, $M=5$. The inner diameters of M ring-shaped photosensitive surfaces from the inside to the outside in the radial direction are the first inner diameter, the second inner diameter, the third inner diameter, the fourth inner diameter and the fifth inner diameter. The first inner diameter may be greater than or equal to 1.2 mm and less than 2 mm, the second inner diameter may be greater than or equal to 2 mm and less than 2.8 mm, the third inner diameter may be greater than or equal to 2.8 mm and less than 3.6 mm, the fourth inner diameter may be greater than or equal to 3.6 mm and less than 4.2 mm, the fifth inner diameter may be greater than or equal to 4.2 mm and less than 6 mm.

In the embodiments of the present disclosure, ring widths of different ring-shaped photosensitive surfaces may be the same or different, which may be provided according to actual conditions, and is not specifically defined here. For example, when $M=3$, the ring width of the ring-shaped photosensitive surface whose inner diameter is the first inner diameter is 0.1 mm, the ring width of the ring-shaped photosensitive surface whose inner diameter is the second inner diameter is 0.2 mm, and the ring width of the ring-shaped photosensitive surface whose inner diameter is the third inner diameter is 0.1 mm.

Optionally, on the basis of the above technical solution, the range of each predetermined wavelength may be greater than or equal to 900 nm or less than or equal to 2400 nm.

In the embodiments of the present disclosure, the range of the predetermined wavelength may substantially cover a near-infrared band. A specific selection of the predetermined wavelength may be determined according to spectral characteristics of the tissue element to be detected, spectral characteristics of the interference component and the individual to be detected.

Optionally, on the basis of the above technical solution, the step 130 may include: from light intensity values in multiple predetermined wavelengths, determining one light intensity value as the light intensity target value of multiple predetermined wavelengths. And the concentration of the tissue element to be detected is determined according to the light intensity target value of multiple predetermined wavelengths.

In the embodiments of the present disclosure, since the effective information carried by the light intensity values at different predetermined distances is different, but the common mode interference information is substantially the same, therefore, the differential operation may be configured to determine the concentration of the tissue element to be detected according to the light intensity values at two different predetermined distances. Through the differential operation, the common mode interference information may be eliminated and the detection accuracy may be improved. Since the light intensity value corresponds to the predetermined distance one by one, two light intensity values may be arbitrarily selected from the light intensity values of multiple predetermined wavelengths as the light intensity measurement value and the light intensity reference value. The light intensity measurement value and the light intensity reference value of multiple predetermined wavelengths are consistent with each other.

After obtaining the light intensity measurement value and the light intensity reference value, the light intensity measurement value and the light intensity reference value may be differentially operated to obtain the differential light intensity value. The differential light intensity value is the differential light intensity values in multiple predetermined wavelengths. The concentration of the tissue element to be detected is determined according to the differential light intensity values in multiple predetermined wavelengths. For the specific operation process, please refer to the patent document with publication number CN1699973A, which will not be repeated here.

Optionally, on the basis of the above technical solution, determining the light intensity measurement value and the light intensity reference value from the light intensity values of multiple predetermined wavelengths, includes: for each predetermined wavelength, according to the predetermined conditions, determining the light intensity measurement value and the light intensity reference value from each light intensity value corresponding to the predetermined wavelength, wherein the predetermined conditions include at least one of the wavelength characteristics, the optical parameters, and the skin structure parameters.

In the embodiments of the present disclosure, the predetermined conditions may be used as a basis for selecting the light intensity measurement value and the light intensity reference value. The predetermined conditions may include at least one of the wavelength characteristics, the optical parameters, and the skin structure parameters. Among them, the optical parameters may include an absorption coefficient, a scattering coefficient, a refractive index and an anisotropy factor, etc. The skin structure parameters may refer to a thickness of the skin tissue.

Optionally, on the basis of the above technical solution, the determining the light intensity measurement value and the light intensity reference value from each light intensity value corresponding to the predetermined wavelength according to the predetermined conditions for each predetermined wavelength, and the predetermined conditions include at least one of wavelength characteristics, optical parameters, and skin structure parameters, which may include: for each predetermined wavelength, according to the variation of light intensity value, determining the light intensity measurement value and the light intensity reference value from each light intensity value corresponding to the predetermined wavelengths, wherein the light intensity measurement value is the light intensity value whose absolute value of the light intensity variation is greater than or equal to the first variation threshold, and the light intensity reference value is the light whose absolute value of the light intensity variation is less than or equal to the second variation threshold. The light intensity variation is the variation between the light intensity value and the corresponding predetermined light intensity value, the first variation threshold is greater than the second variation threshold, and the predetermined light intensity value is the light intensity value emitted from the surface of the detected site when the predetermined light intensity value is the concentration of the tissue element to be detected.

In the embodiments of the present disclosure, on the basis of improving the detection accuracy by improving the light receiving efficiency described above, in order to further improve the detection accuracy, based on the floating reference theory, for the predetermined wavelength, the light intensity measurement value and the light intensity reference value are determined from light intensity values in multiple predetermined wavelengths, and the concentration of the tissue element to be detected is determined according to the light intensity measurement value and the light intensity reference value of multiple predetermined wavelengths. Based on the floating reference theory, for the predetermined wavelength, the light intensity measurement value and light intensity reference value are determined from each light intensity value under the predetermined wavelength, specifically, the light intensity variation may be understood as the light intensity variation between the light intensity value and the corresponding predetermined light intensity value. The predetermined light intensity value may be understood as an obtained light intensity value emitted from the surface of the detected site when the concentration of the tissue element to be detected is the predetermined concentration. The light intensity measurement value may be the light intensity value whose absolute value of the light intensity variation is greater than or equal to the first variation threshold, and the light intensity reference value may be the light intensity value whose absolute value of the light intensity variation is less than or equal to the second variation threshold. Wherein, the specific numerical values of the first variation threshold and the second variation threshold may be provided according to actual conditions, and are not specifically limited here.

The light intensity reference value reflects the response of other interferences other than the tissue element to be detected during the detection process. The light intensity measurement value reflects the response of the tissue element to be detected and the response of other interferences other than the tissue element to be detected. The response that reflects interferences other than the tissue element to be detected during the detection process may be regarded as interference information, and the response of the tissue element to be detected may be regarded as effective information. Therefore, the light intensity reference value includes the interference information, and the light intensity measurement value includes the interference information and the effective information. According to the light intensity reference value and the light intensity measurement value, the common mode interference information is eliminated to improve the detection accuracy.

Optionally, on the basis of the above technical solution, determining the concentration of the tissue element to be detected according to the light intensity measurement value and light intensity reference value of multiple predetermined wavelengths, includes: for each predetermined wavelength, performing the differential operation on the light intensity measurement value and the light intensity reference value corresponding to the predetermined wavelength to obtain the differential light intensity value. The concentration of the tissue element to be detected is determined according to the differential light intensity values in multiple predetermined wavelengths.

In the embodiments of the present disclosure, for each predetermined wavelength, the light intensity reference value and the light intensity measurement value under the predetermined wavelength may be differentially operated to obtain the differential light intensity value. Based on this, the differential light intensity values in multiple predetermined wavelengths may be obtained. Each differential light intensity values in multiple predetermined wavelengths may be input as an input variable into a tissue element concentration prediction model generated by pre-training to obtain a prediction result, which is the concentration of the tissue element to be detected. For the specific calculation process, please refer to the patent document with publication number CN1699973A, which will not be repeated here. The above-mentioned differential operation eliminates the common mode interference information in the light intensity reference value and the light intensity measurement value, thereby improving the detection accuracy.

Optionally, on the basis of the above-mentioned technical solution, before the step 120, the method may further include: shielding interference light.

In the embodiments of the present disclosure, after the incident light is transmitted to the detected site, a part of the incident light will be directly reflected on the surface of the detected site to form surface reflected light, and a part of the incident light will form the diffuse-scattered light as described above. Among them, since the surface reflected light has no effect on the tissue and will not carry the effective information, the surface reflected light may be used as the interference light. In addition, there is diffracted light. Similarly, since the diffracted light has no effect on the tissue, it will not carry the effective information. Therefore, the diffracted light may be used as the interference light. That is, the interference light may include the diffracted light, and the surface reflected light generated by the incident light passing through the surface of the detected site. Since the diffuse-scattered light interacts with skin tissue and carries the effective information, the diffusely-scattered light may be used as the effective light.

Based on the above, in order to further improve the detection accuracy, before the step 120, the interference light may be shielded, so that the light intensity value emitted from the surface of the detected site is the light intensity value corresponding to the diffusely-scattered light, and the light intensity value corresponding to the surface reflected light and the light intensity value corresponding to the diffracted light are eliminated.

In the above, the interference light is shielded before the light intensity value emitted from the surface of the detected site is obtained, thereby eliminating the light intensity value corresponding to the interference light in the light intensity values, and retaining the light intensity value corresponding to the diffusely-scattered light in the light intensity values. Since the diffusely-scattered light carries the effective information, and the interference light does not carry the effective information, the detection accuracy is further improved.

Figure 6:
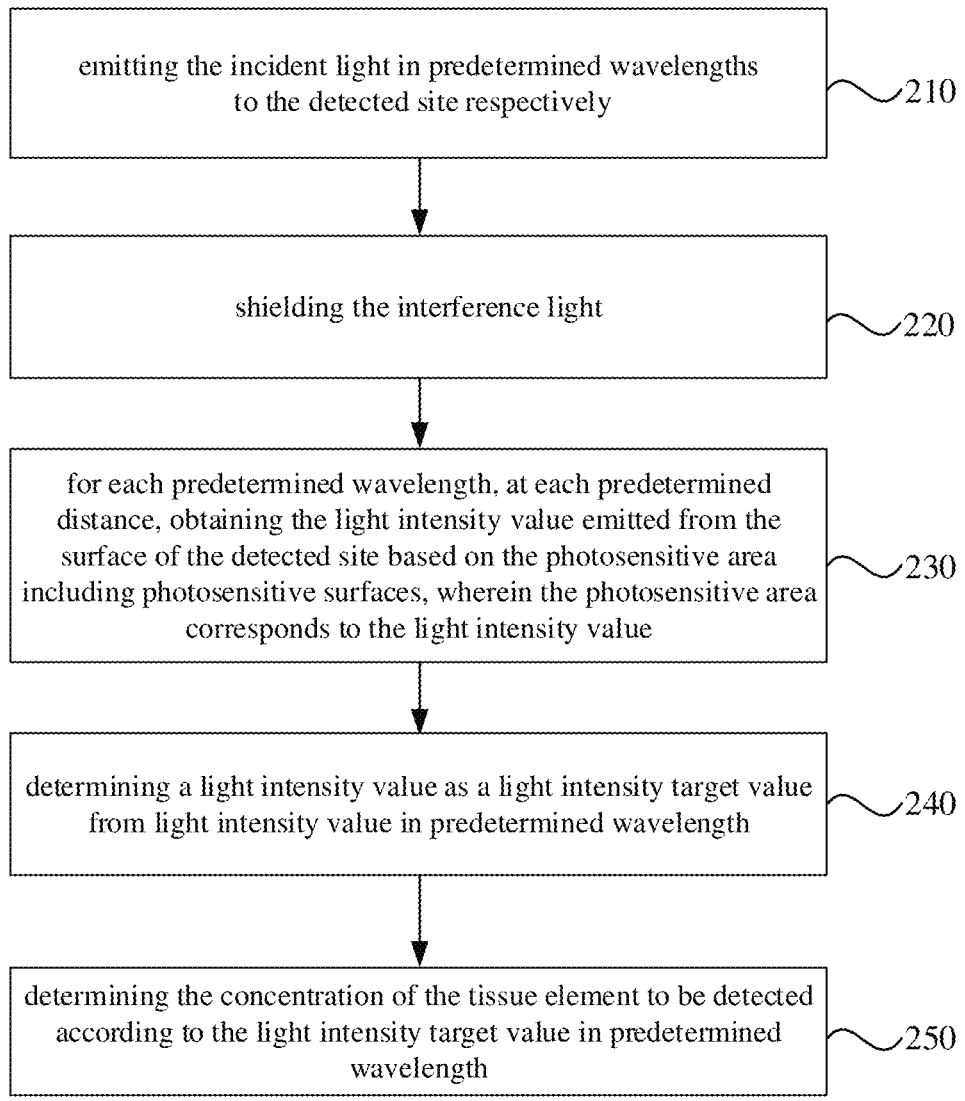
FIG. 6 is a flow chart of another non-invasive detection method for tissue element according to embodiments of the present disclosure.

FIG. 6 is a flowchart of another non-invasive detection method for the tissue element provided by the embodiments of the present disclosure. As shown in FIG. 6, the method specifically includes the following steps.

In step 210, the incident light of multiple predetermined wavelengths is emitted to the detected site, respectively.

In step 220, the interference light is shielded.

In step 230, for each predetermined wavelength and at each predetermined distance, the light intensity value emitted from the surface of the detected site is obtained based on the photosensitive area including each photosensitive surface, and the photosensitive area is in one-to-one correspondence with the light intensity value.

In step 240, a light intensity value is determined from light intensity values in multiple predetermined wavelengths as the light intensity target value of multiple predetermined wavelengths.

In step 250, the concentration of the tissue element to be detected is determined according to the light intensity target value of multiple predetermined wavelengths.

The technical solution of this embodiment obtains the light intensity value emitted from the surface of the detected site based on the photosensitive area including each photosensitive surface at each predetermined distance, thereby improving the efficiency of receiving homogeneous scattered light, and improving the detection accuracy of the tissue element to be detected. On this basis, differential operations may be performed according to the light intensity values obtained from different ring-shaped photosensitive areas, which eliminates the common-mode interference information and improves the detection accuracy of the tissue element to be detected.

Figure 7:
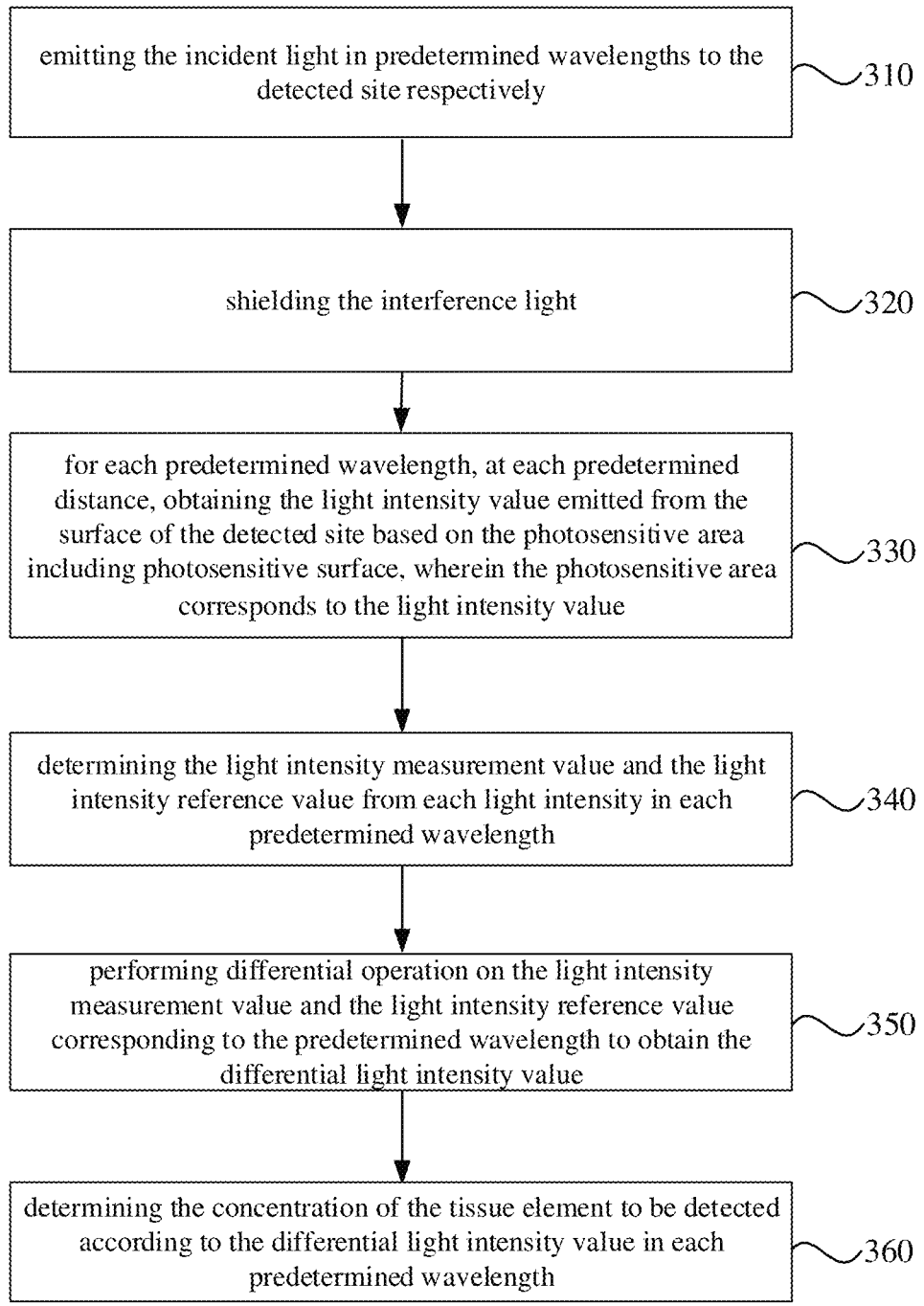
FIG. 7 is a flow chart of yet another non-invasive detection method for tissue element according to embodiments of the present disclosure.

FIG. 7 is a flowchart of yet another non-invasive detection method of the tissue element according to the embodiments of the present disclosure. As shown in FIG. 7, the method specifically includes the following steps.

In step 310, the incident light of multiple predetermined wavelengths is emitted to the detected site, respectively.

In step 320, the interference light is shielded.

In step 330, for each predetermined wavelength and at each predetermined distance, the light intensity value emitted from the surface of the detected site is obtained based on the photosensitive area including each photosensitive surface, the photosensitive area is in one-to-one correspondence with the light intensity value, and there is at least one predetermined distance.

In step 340, the light intensity measurement value and the light intensity reference value are determined from light intensity values in multiple predetermined wavelengths.

In step 350, the differential operation is performed on the light intensity measurement value and the light intensity reference value corresponding to the predetermined wavelength to obtain the differential light intensity value.

In step 360, the concentration of the tissue element to be detected is determined according to the differential light intensity values in multiple predetermined wavelengths.

The technical solution of this embodiment obtains the light intensity value emitted from the surface of the detected site based on the photosensitive area including each photosensitive surface at each predetermined distance, thereby improving the efficiency of receiving homogeneous scattered light, and improving the detection accuracy of the tissue element to be detected. On this basis, differential operations may be performed according to the light intensity values obtained from different ring-shaped photosensitive areas, which eliminates the common-mode interference information and improves the detection accuracy of the tissue element to be detected.

Figure 8:
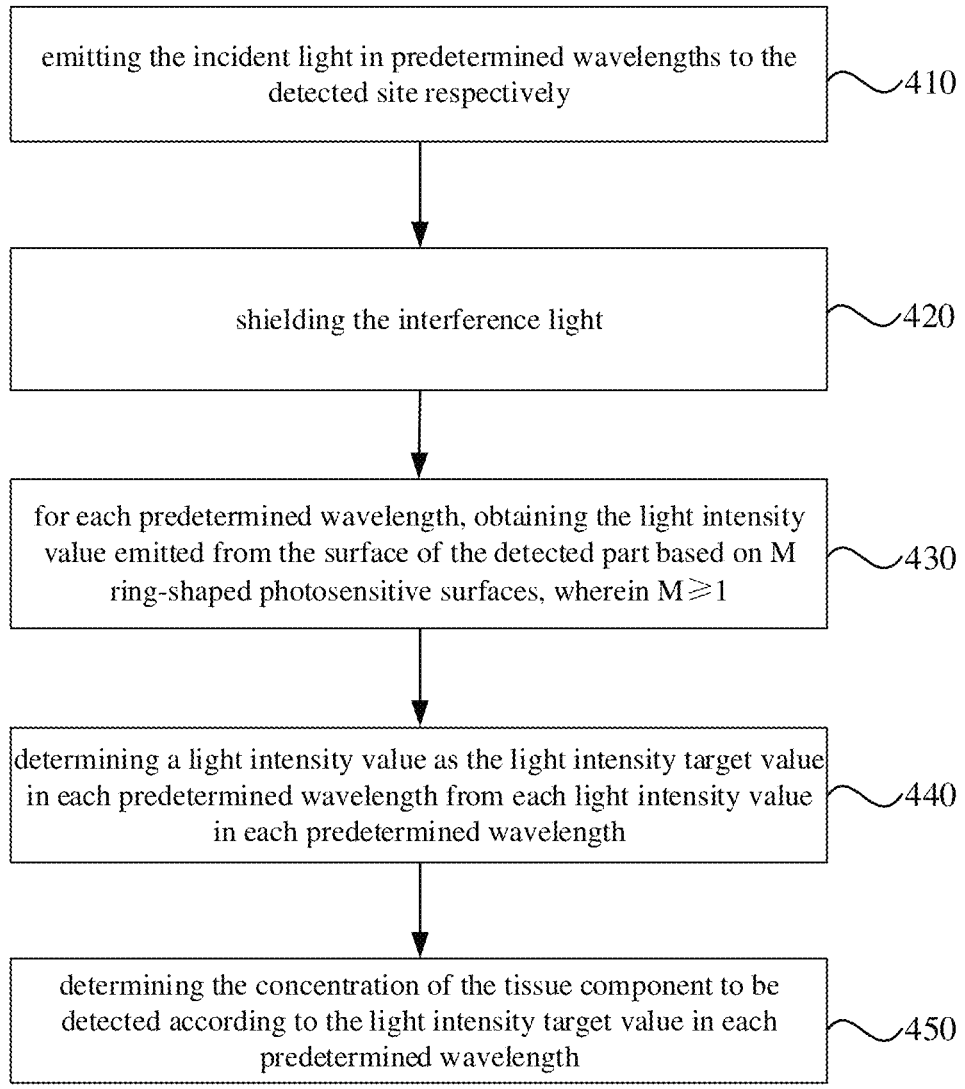
FIG. 8 is a flow chart of another non-invasive detection method for tissue element according to embodiments of the present disclosure.

FIG. 8 is a flowchart of another non-invasive detection method for the tissue element according to the embodiments of the present disclosure. As shown in FIG. 8, the method specifically includes the following steps.

In step 410, the incident light of multiple predetermined wavelengths is emitted to the detected site, respectively.

In step 420, the interference light is shielded.

In step 430, for each predetermined wavelength, the light intensity value emitted from the surface of the detected site is obtained based on the M ring-shaped photosensitive surfaces, and each ring-shaped photosensitive surface is in one-to-one correspondence with the light intensity value, where $M \geq 1$.

In step 440, the light intensity value is determined from light intensity values in multiple predetermined wavelengths as the light intensity target value of multiple predetermined wavelengths.

In step 450, the concentration of the tissue element to be detected is determined according to the light intensity target value of multiple predetermined wavelengths.

The technical solution of this embodiment obtains the light intensity value emitted from the surface of the detected site based on M ring-shaped photosensitive surfaces at each predetermined distance, thereby improving the efficiency of receiving the homogeneous scattered light, thereby improving the detection accuracy of the tissue element to be detected. On this basis, differential operations may be performed based on the light intensity values obtained from different ring-shaped photosensitive areas, which eliminates the common mode interference information and improves the detection accuracy of the tissue element to be detected.

Figure 9:
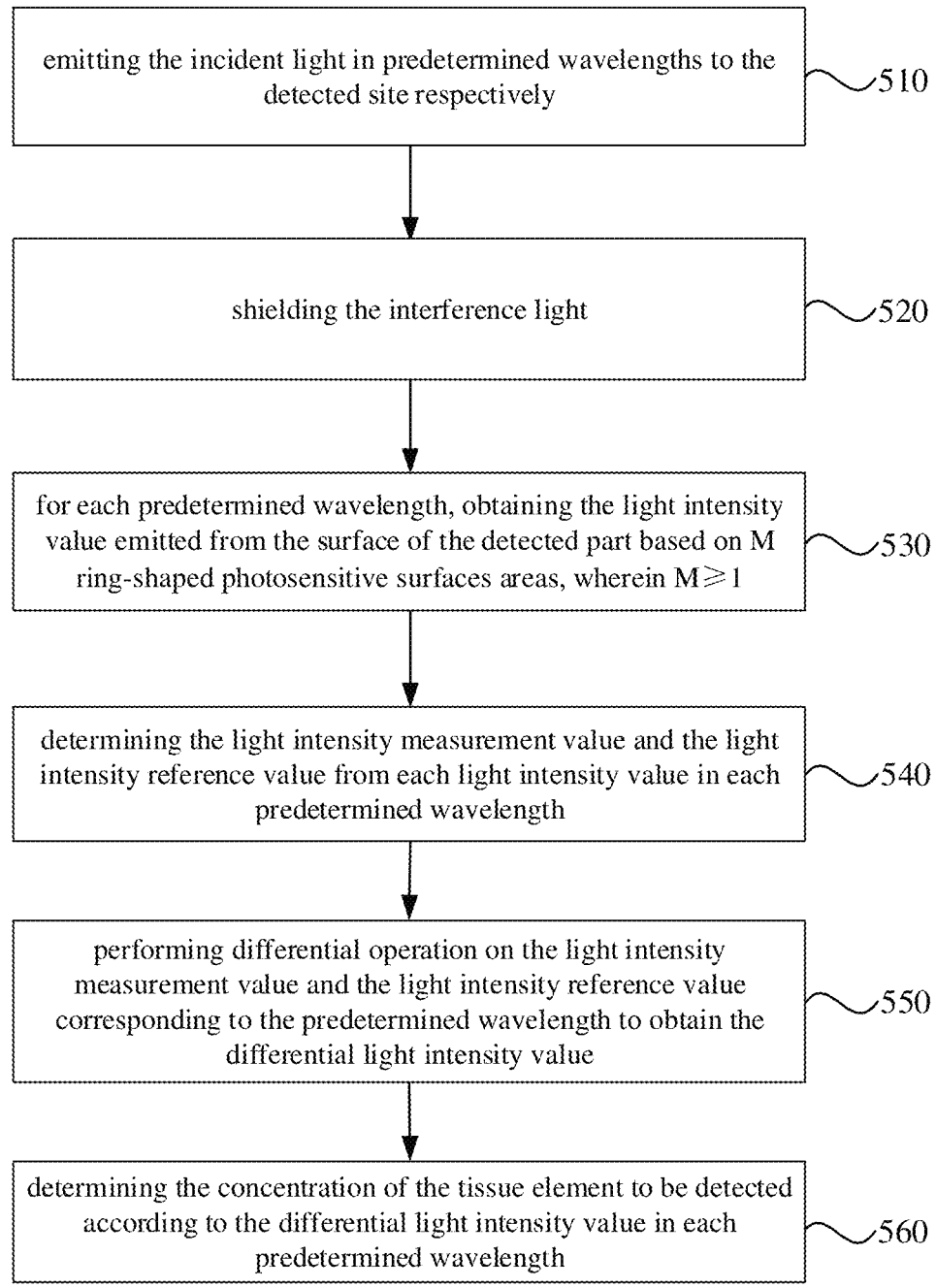
FIG. 9 is a flow chart of another non-invasive detection method for tissue element according to embodiments of the present disclosure.

FIG. 9 is a flowchart of another non-invasive detection method for the tissue element according to the embodiments of the present disclosure. As shown in FIG. 9, the method specifically includes the following steps.

In step 510, the incident light of multiple predetermined wavelengths is emitted to the detected site, respectively.

In step 520, the interference light is shielded.

In step 530, for each predetermined wavelength, the light intensity value emitted from the surface of the detected site is obtained based on the M ring-shaped photosensitive surfaces, and each ring-shaped photosensitive surface is in one-to-one correspondence with the light intensity value, where M≥1.

In step 540, the light intensity measurement value and the light intensity reference value are determined from light intensity values in multiple predetermined wavelengths.

In step 550, the differential operation is performed on the light intensity measurement value and the light intensity reference value corresponding to the predetermined wavelength to obtain the differential light intensity value.

In step 560, the concentration of the tissue element to be detected is determined according to the differential light intensity values of multiple predetermined wavelengths.

The technical solution of this embodiment obtains the light intensity value emitted from the surface of the detected site based on the M ring-shaped photosensitive surfaces, thereby improving the efficiency of receiving the homogeneous scattered light, thereby improving the detection accuracy of the tissue element to be detected. On this basis, differential operations may be performed based on the light intensity values obtained from different ring-shaped photosensitive areas, which eliminates the common mode interference information and improves the detection accuracy of the tissue element to be detected.

It should be noted that, the above steps 220, 320, 420 and 520 only need to be performed before the corresponding steps 230, 330, 430 and 530.

The non-invasive detection method for the tissue element provided by the embodiments of the present disclosure may provide a non-invasive detection device for tissue element, the non-invasive detection device for tissue element may be realized by manners such as software and/or hardware, and the non-invasive detection device for the tissue element may be worn to a wearable apparatus, such as a smart watch.

Figure 10:
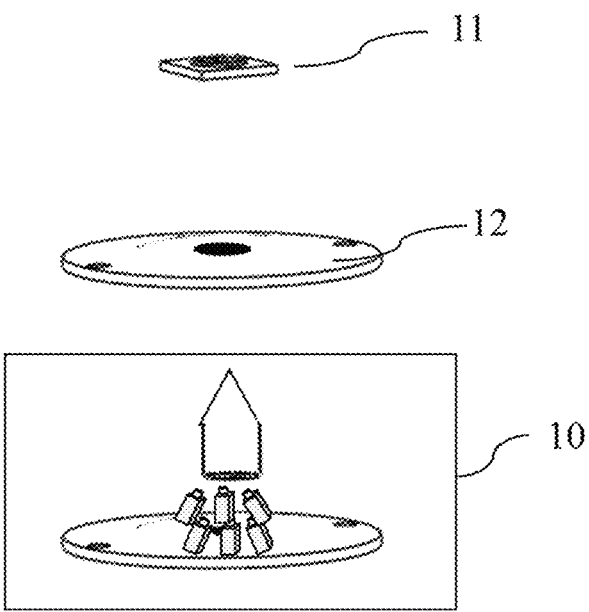
FIG. 10 is a schematic structural diagram of a non-invasive detection device for tissue element according to the embodiments of the present disclosure.

FIG. 10 is a schematic structural diagram of a non-invasive detection device for tissue element provided by the embodiments of the present disclosure. This embodiment may be suitable for improving the detection accuracy of concentration of the tissue element to be detected. As shown in FIG. 10, the non-invasive detection device 1 for tissue element may include a light source module 10, a detection module 11 and a processing module 12. The detection module 11 may be in communication with the processing module 12. The structure and working principle are described below in conjunction with the drawings.

The light source module 10 may be configured to respectively emit the incident light of multiple predetermined wavelengths to the detected site.

The detection module 11 may be configured to obtain the light intensity value emitted from the surface of the detected site based on multiple photosensitive surfaces for each predetermined wavelength, and emit each light intensity value to the processing module 12, and multiple photosensitive surfaces are located at corresponding predetermined distances from the canter of the incident light.

The processing module 12 may be configured to determine the concentration of the tissue element to be detected according to the light intensity values in each predetermined wavelength.

In the embodiment of the present disclosure, the light source module 10 may emit the incident light to the detected site. Among them, the light source module 10 has the following two forms: one of which is a module that the light source module 10 may directly emit the incident light; second of which is that the light source module 10 may be a medium that transmits the incident light, such as an optical fiber, through which the incident light emitted form external light source is emitted to the detected site.

For each predetermined wavelength, at each photosensitive surface, the detection module 11 may obtain the light intensity value emitted from the surface of the detected site, and send each light intensity value to the processing module 12. The detection module 11 may include at least one photosensitive surface 111. In order to improve the receiving efficiency of homogeneous scattered light, this may be achieved in the following manner: for each predetermined distance, at least one photosensitive surface 111 may be provided, and the anodes of different photosensitive surfaces 111 at a same predetermined distance are connected. The detection module 11 may be configured to obtain the light intensity value emitted from the surface of the detected site through the detection of the photosensitive area including photosensitive surfaces at each predetermined distance. The photosensitive area is in one-to-one correspondence with the light intensity value. The number of the predetermined distances is at least one. The photosensitive surface 111 may be an annular photosensitive surface 1110.

In addition, since the detection module 11 may directly obtain the light intensity value emitted from the detected site, a light loss is reduced, and the detection efficiency is improved.

The processing module 12 may determine the concentration of the tissue element to be detected according to each light intensity value in multiple predetermined wavelengths. For each light intensity value in each predetermined wavelength, the determination of the concentration of the tissue element to be detected may refer to the description of the corresponding part of the non-invasive detection method for the tissue element above, which will not be repeated here.

Since the technical solution of this embodiment may achieve a wide range of light intensity value reception, the light receiving efficiency is improved, and the detection accuracy of the tissue element to be detected is further improved. Since the detection module may directly process the light intensity value emitted from the detected site, the light loss is reduced and the detection efficiency is improved.

Due to the substantial reduction in a volume of the detection device, the detection device is easy to be worn and fixed on the detected site, which may ensure a stability of the detection conditions, correspondingly, improve the stability of the detection conditions, and in addition, realize a portable detection. On this basis, since different light intensity values may be used for the differential operation, the common mode interference information may be eliminated, and therefore, the detection accuracy of the tissue element to be detected is also improved.

Figure 11:
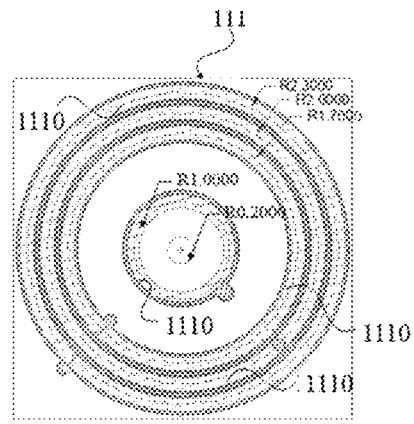
FIG. 11 is a schematic structural diagram of a detection module according to the embodiments of the present disclosure.

Optionally, as shown in FIG. 11, on the basis of the above technical solution, the detection module 11 may include at least one photosensitive surface 1110. Anodes of different photosensitive surfaces 1110 at the same predetermined distance are connected.

For each predetermined distance, at least one photosensitive surface 111 is provided.

The detection module 11 may be used at each predetermined distance, to obtain the light intensity value emitted from the surface of the detected site based on the photosensitive area including photosensitive surface 111, and the photosensitive are is in one-to-one correspondence with the light intensity value.

In the embodiments of the present disclosure, in order to improve the receiving efficiency of homogeneous light, at least one photosensitive surface 111 may be provided for each predetermined distance. Anodes of different photosensitive surfaces 111 at the predetermined distance are connected. The description for the photosensitive surface may refer to the description above for the photosensitive surface, which will not be repeated here.

As mentioned above, at least one photosensitive surface 111 is provided at the same predetermined distance, and each photosensitive surface 111 at the predetermined distance corresponds to one source-detection distance, thereby improving the efficiency of receiving homogeneous scattered light.

Optionally, as shown in FIG. 11, based on the foregoing technical solution, each photosensitive surface 111 is an annular photosensitive surface 1110. The different ring-shaped photosensitive surfaces 1110 are arranged in a same geometric center, and the number of the ring-shaped photosensitive surfaces 1110 may be M, where M≥1.

In the embodiments of the present disclosure, each photosensitive surface 111 may be an annular photosensitive surface 1110. Each annular photosensitive surface 1110 corresponds to a source-detection distance. As mentioned above, by arranging the photosensitive surface 111 of the detection module 11 into a ring-shaped structure with different inner diameters, each ring-shaped photosensitive surface corresponds to a source-detection distance, which maximizes the reception of homogeneous scattered light, thereby improving the efficiency of receiving the homogeneous scattered light.

Optionally, based on the above technical solution, an inner diameter of each annular photosensitive surface 1110 may be greater than or equal to 0.5 mm and less than or equal to 6 mm, and a ring width of each annular photosensitive surface 1110 may be greater than or equal to 0.05 mm and less than or equal to 0.3 mm.

Optionally, on the basis of the above technical solution, when M=4, the inner diameters of M ring-shaped photosensitive surfaces from inside to outside in a radial direction are the first inner diameter, the second inner diameter, the third inner diameter and the fourth inner diameter, respectively. The first inner diameter is greater than or equal to 1.2 mm and less than 3 mm, the second inner diameter is greater than or equal to 3 mm and less than 3.8 mm, the third inner diameter is greater than or equal to 3.8 mm and less than 4.4 mm, the fourth inner diameter is greater than or equal to 4.4 mm and less than 6 mm. Alternatively, when M=5, the inner diameters of M ring-shaped photosensitive surfaces from inside to outside in the radial direction are the first inner diameter, the second inner diameter, the third inner diameter, the fourth inner diameter and the fifth inner diameter, respectively; the first inner diameter is greater than or equal to 1.2 mm and less than 2 mm, the second inner diameter is greater than or equal to 2 mm and less than 2.8 mm, the third inner diameter is greater than or equal to 2.8 mm and less than 3.6 mm, the fourth inner diameter is greater than or equal to 3.6 mm and less than 4.2 mm, and the fifth inner diameter is greater than or equal to 4.2 mm and less than 6 mm.

Optionally, the ring width of each ring-shaped photosensitive surface is 0.1 mm or 0.2 mm.

Optionally, on the basis of the above technical solution, a range of each predetermined wavelength may be greater than or equal to 900 nm and less than or equal to 2400 nm.

In the embodiments of the present disclosure, each ring-shaped photosensitive surface 1110 may correspond to one ring-shaped photosensitive surface. For the size of the aforementioned ring-shaped photosensitive surface 1110 and the number of the ring-shaped photosensitive surfaces 1110, please refer to the above description of the ring-shaped photosensitive surface, which will not be repeated here. In addition, the description of the wavelength range of the incident light may also refer to the description of the corresponding part above, which will not be repeated here, neither.

Figure 12:
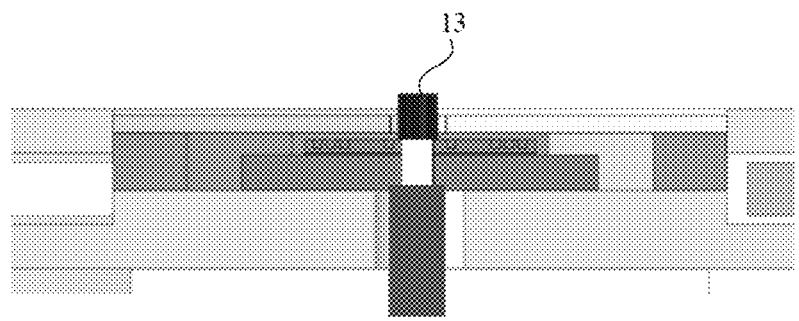
FIG. 12 is a schematic structural diagram of a first sleeve according to the embodiments of the present disclosure.

Optionally, as shown in FIG. 12, based on the above technical solution, the non-invasive detection device 1 for tissue element may further include a first sleeve 13. The first sleeve 13 may be disposed on an upper surface of the detection module 11, and the inner diameter of the first sleeve 13 may be larger than a diameter of an aperture on the detection module 11.

The first sleeve 13 is used to prevent the surface reflection light, that is generated on the surface of the detected site, from entering the detection module 11 and to prevent the diffracted light, that is generated by incident light passing through the aperture of the detection module 11, from entering the detection module 11.

Figure 13:
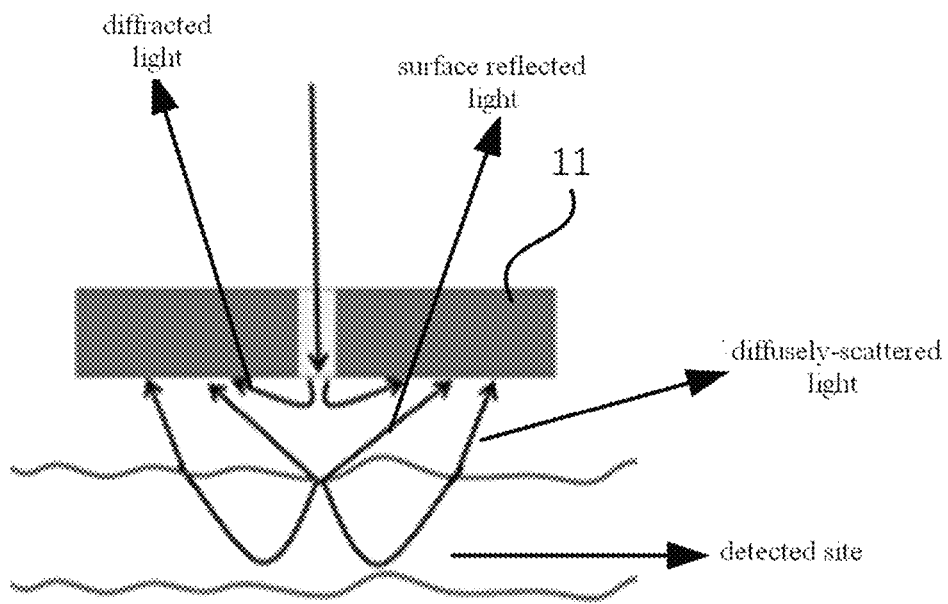
FIG. 13 is a schematic diagram of a transmission of incident light according to the embodiments of the present disclosure.

In the embodiments of the present disclosure, as shown in FIG. 13, a part of the incident light will be directly reflected on the surface of the detected site to form the surface reflected light. Since the surface reflected light does not carry the effective information, when there is a light intensity value corresponding to the surface reflected light in the light intensity values obtained by the detection module 11, the detection accuracy is reduced. In addition, the incident light passing through the aperture of the detection module 11 generates the diffracted light, and the diffracted light does not carry the effective information, therefore, when there is a light intensity value corresponding to the surface reflected light in the light intensity value obtained by the detection module 11, the detection accuracy is reduced. In order to prevent the surface reflected light from entering the detection module 11, a first sleeve 13 may be provided on the upper surface of the detection module 11. The inner diameter of the first sleeve 13 may be larger than a diameter of the aperture on the detection module 11. Both the surface reflected light and the diffracted light will be blocked by the first sleeve 13 and will not be received by the detection module 11.

Figure 14:
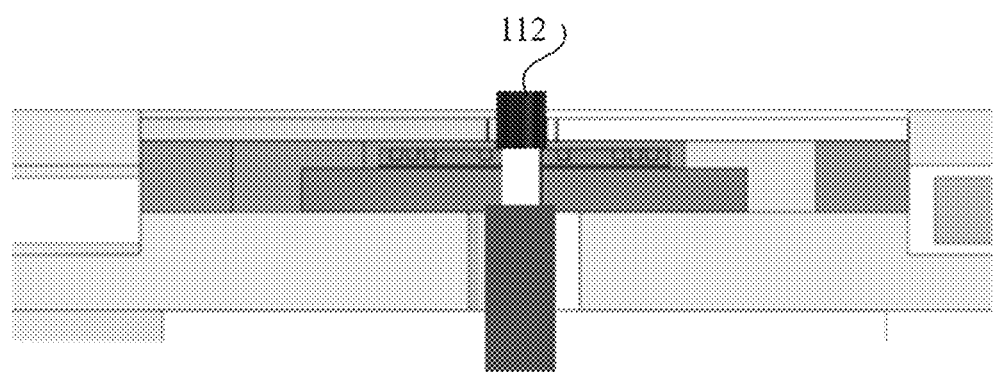
FIG. 14 is a schematic structural diagram of a second sleeve according to the embodiments of the present disclosure.

Optionally, as shown in FIG. 14, on the basis of the above technical solution, the detection module 11 may also be provided with a second sleeve 112 that is integrally connected. The second sleeve 112 may be disposed on the upper surface of the detection module 11, and an inner diameter of the second sleeve 112 may be larger than the diameter of the aperture on the detection module 11.

The second sleeve 112 may be configured to prevent the surface reflected light generated from the surface of the detected site from entering the detection module 11 and to prevent the diffracted light generated by incident light passing through the aperture of the detection module 11 from entering the detection module 11.

In the embodiments of the present disclosure, in order to prevent the surface reflected light and the diffracted light from entering the detection module 11, in addition to providing the first sleeve 13 on the upper surface of the detection module 11, the second sleeve 112 may be directly provided on the upper surface of the detection module 11 when manufacturing the detection module 11, that is, the second sleeve 112 is a part of the detection module 11. Wherein, the inner diameter of the second sleeve 112 may be larger than the diameter of the aperture on the detection module 11.

Figure 15:
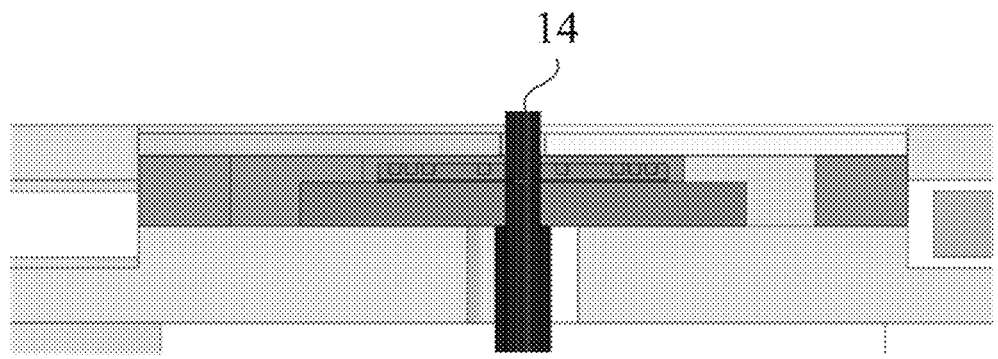
FIG. 15 is a schematic structural diagram of a third sleeve according to the embodiments of the present disclosure.

Optionally, as shown in FIG. 15, based on the above technical solution, the non-invasive detection device 1 for tissue element may further include a third sleeve 14. An upper surface of the third sleeve 14 may pass through the aperture of the detection module 11 and exceed the upper surface of the detection module 11.

The third sleeve 14 may be configured to prevent the surface reflected light, that is generated from the surface of the detected site, from entering the detection module 11 and to prevent the diffracted light, that is generated by incident light passing through the aperture of the detection module 11, from entering the detection module 11.

In the embodiments of the present disclosure, in order to prevent the surface reflected light and the diffracted light from entering the detection module 11, in addition to the above two sleeves, a third sleeve 14 may be provided, and the upper surface of the third sleeve 14 may pass through the aperture of the detection module 11 and exceed the upper surface of the detection module 11. An outer diameter of the third sleeve 14 may be smaller than the diameter of the aperture on the detection module 11.

For the first sleeve 13 and the second sleeve 112 as described above, whether the aperture on the detection module 11 is open may be provided according to actual situations, which are not specifically limited here. No matter whether the aperture on the detection module 11 is open or not, light may pass through. In addition, the second sleeve 112 will increase the difficulty of manufacturing the detection module 11. Compared with the first sleeve 13, the third sleeve 14 has a simpler implementation form. The above-mentioned type of sleeve may be selected according to actual conditions to prevent the surface reflected light and the diffracted light from entering the detection module 11, which is not specifically limited here.

Figure 16:
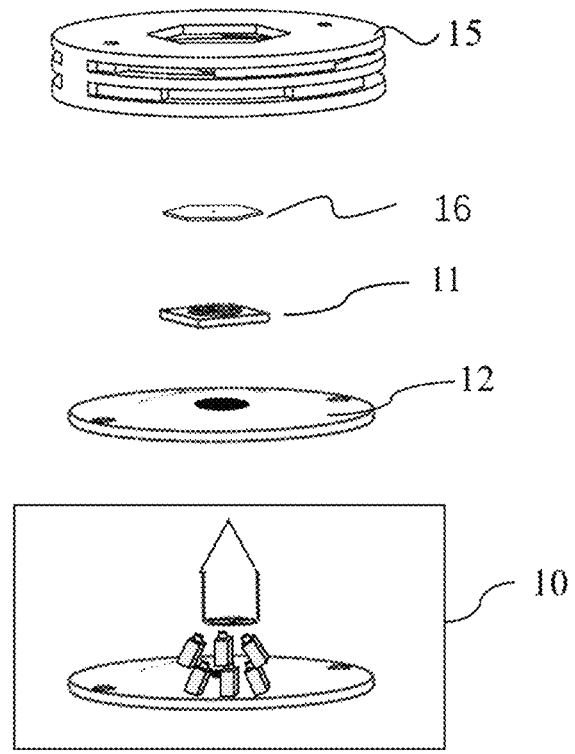
FIG. 16 is a schematic structural diagram of another non-invasive detection device for tissue element according to the embodiments of the present disclosure.

Optionally, as shown in FIG. 16, based on the above technical solution, the non-invasive detection device 1 for tissue element may further include a housing 15. The light source module 10, the detection module 11 and the processing module 12 may be disposed inside the housing 15, and the upper surface of the detection module 11 may be lower than the upper surface of the housing 15.

In the embodiments of the present disclosure, in order to realize the detection of the tissue element using the non-invasive detection device 1 for tissue element is a non-contact detection, that is, the upper surface of the detection module 11 is not in contact with the surface of the detected site, the upper surface of the detection module 11 may be provided to be lower than the upper surface of the housing 15.

It should be noted that, the upper surfaces of the first sleeve 13, the second sleeve 112 and the third sleeve 14 may exceed the upper surface of the housing 15.

Optionally, as shown in FIG. 16, based on the above technical solution, the non-invasive detection device 1 for tissue element may further include a protection member 16. The protection member 16 may be arranged at the aperture on the upper surface of the housing 15, and the upper surface of the protection member 16 may be lower than the upper surface of the housing 15, and the protection member 16 may be provided with an aperture and may be arranged in the same geometric center as the housing 15. A light transmittance of the protection member 16 may be greater than or equal to a light transmittance threshold.

The protection member 16 may be configured to protect the detection module 11, and when the non-invasive detection device 1 for tissue element is worn to the detected site, it may ensure that the skin condition of the detected site remains in a natural state, so as to realize the non-contact detection.

In the embodiments of the present disclosure, in order to protect the detection module 11 from dust attachment and human touch, a protection member 16 may be provided at the aperture of the housing 15. Wherein, the protection member 16 may also be provided with an aperture, and the protection member 16 may be disposed in the same geometric center as the housing 15, and the upper surface of the protection member 16 may be lower than the upper surface of the housing 15. Moreover, since the detection module 11 is not in direct contact with the detected site, it may ensure that the skin condition of the detected site remains in the natural state and realize a non-contact detection. In addition, the non-contact detection may also reduce a time to reach a thermal equilibrium state.

A material of the protection member 16 may be a material whose transmittance is greater than or equal to the light transmittance threshold. The light transmittance threshold may be 0.6. Optionally, the protection member 16 may be a quartz glass sheet. If the incident light is near-infrared light, the material discharged into the quartz glass may be JGS1S. A T-shaped hole, such as a regular hexagon, may be provided in a center of the above-mentioned housing 15 for placing a quartz glass sheet. The quartz glass sheet may be provided with an aperture in the center, and a diameter of the aperture on the quartz glass sheet is slightly greater than the outer diameters of the first sleeve 13 and the second sleeve 1117. In addition, grooves may be provided around the housing 15 to realize heat dissipation.

Figure 17:
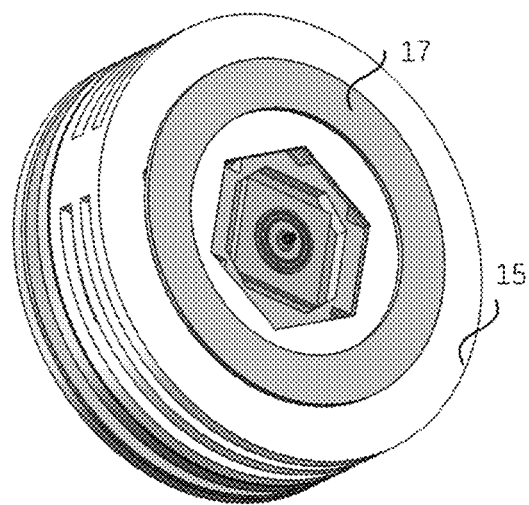
FIG. 17 is a schematic structural diagram of a contact member according to the embodiments of the present disclosure.

Optionally, as shown in FIG. 17, based on the above technical solution, the non-invasive detection device 1 for tissue element may further include a contact member 17. The contact member 17 may be provided on the upper surface of the housing 15, and a thermal conductivity of a material of the contact member 17 may be within a range of air thermal conductivity.

The contact member 17 may be configured to ensure that the skin condition of the detected site remains in a natural state when the non-invasive detection device 1 for tissue element is worn to the detected site, to realize the non-contact detection, and by setting the thermal conductivity of the thermal insulation material within the range of air thermal conductivity, the time for the heat conduction between the non-invasive detection device 1 for tissue element to be worn to the detected site and the detected site to reach a thermal equilibrium state is reduced.

In the embodiments of the present disclosure, after wearing the non-invasive detection device 1 for tissue element, the detected site may reach the thermal equilibrium state as quickly as possible, it is required to reduce the time for the heat conduction between the detected site and the non-invasive detection device 1 for tissue element to reach the thermal equilibrium state. The contact member 17 may be provided on the upper surface of the housing 15, and the thermal conductivity of the material of the contact member 17 needs to be within the range of air thermal conductivity. The air thermal conductivity may be greater than 0.01 W/mK and less than or equal to 0.4 W/mK. Exemplarily, if the contact member 17 is not used, the time to reach the thermal equilibrium state is about 1 hour. If the thermal conductivity of the material of the contact member 17 is 0.14 W/mK, the time to reach the thermal equilibrium state is 0.25 hours. If the thermal conductivity of the material of the contact member 17 is 0.4 W/mK, the time to reach the thermal equilibrium state is about 0.3 hours. It may be seen that, compared with not using the contacting member 17, the time to reach the thermal equilibrium state may be reduced by using the contacting member 17 and setting the thermal conductivity of the material of the contact member 17 within the range of air thermal conductivity. Moreover, since the detection module 11 is not in direct contact with the detected site, it may ensure that the skin condition of the detected site remains in the natural state and realize the non-contact detection. In addition, the non-contact detection may also reduce the time to reach the thermal equilibrium state.

It should be noted that, in order to ensure that the thermal conductivity of the material is within the air thermal conductivity range, the material of the contact member 17 may include silica gel, polyvinyl chloride, and the like. The contact member 17 may be an interface pad. A shape of the interface pad may include ring and square frame, etc. The shape and a size of the interface pad may be provided according to actual conditions, and are not specifically limited here.

Optionally, on the basis of the above technical solution, the upper surface of the housing 15 may be plated with a heat-insulating material, and a thermal conductivity of the heat-insulating material may be within the range of air thermal conductivity.

The thermal insulation material may be configured to ensure that the skin condition of the detected site remains in the natural state when the non-invasive detection device 1 for tissue element is worn to the detected site, to achieve the non-contact detection. Moreover, by setting the thermal conductivity of the thermal insulation material within the range of air thermal conductivity, the time for the heat conduction between the non-invasive detection device 1 tissue element to be worn to the detected site and the detected site to reach the thermal equilibrium state is reduced.

In the embodiments of the present disclosure, similarly to the contact member 17, a heat insulating material may be plated directly on the upper surface of the housing 15, and the thermal conductivity of the heat insulating material may be within the range of air thermal conductivity. The air thermal conductivity may be greater than 0.01 W/mK and less than or equal to 0.4 W/mK in the range of air thermal conductivity. The heat insulating material may be silica gel, polyvinyl chloride, etc.

Optionally, based on the above technical solution, the light source module 10 may include a light source emitting unit or an incident optical fiber.

In the embodiments of the present disclosure, the light source module 10 may include a light source emitting unit or an incident optical fiber. If the light source module 10 includes a light source emitting unit, the incident light may be directly emitted to the detected site by the light source emitting unit. If the light source module 10 includes an incident optical fiber, the incident light may be emitted to the detected site through the incident optical fiber. Wherein, the incident light is generated by external light source.

As mentioned above, if the light source module 10 includes a light source emitting unit, compared with the light source module 10 including an incident optical fiber, a volume of the non-invasive detection device 1 for tissue element will become larger. However, the light source emitting unit is included inside, the incident optical fiber is not necessary to transmit the incident light, which produces optical loss, therefore, the optical loss is smaller, and it may avoid the interference caused by an introduction of optical fiber. On the contrary, if the light source module 10 includes the incident optical fiber, compared with the light source module 10 including the light source emitting unit, the volume of the tissue element non-invasive detection device 1 will be reduced. However, since the incident light is transmitted through the incident optical fiber, the optical fiber transmission generates light loss, the light loss is greater, and the optical fiber is easily affected by external environment to cause interference. Whether the light source module 10 includes the light source emitting unit or the incident optical fiber may be provided according to actual conditions, which is not limited here.

It should be noted that, the upper surfaces in the embodiments of the present disclosure refer to the surfaces close to the detected site, and the lower surface refer to the surface away from the detected site.

Figure 18:
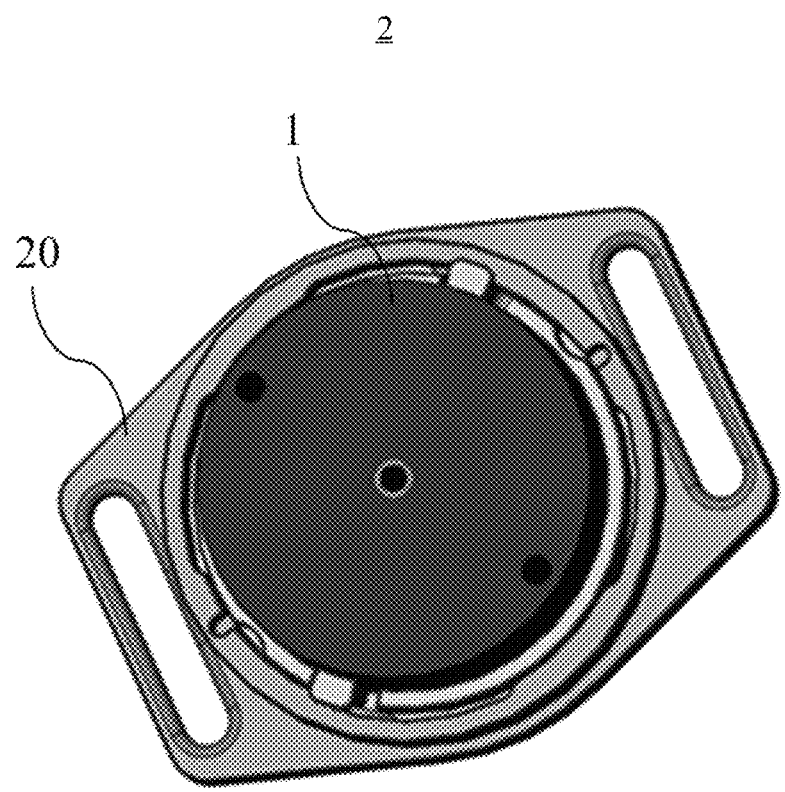
FIG. 18 is a schematic structural diagram of a wearable apparatus according to the embodiments of the present disclosure.

FIG. 18 is a schematic structural diagram of a wearable apparatus provided by the embodiments of the present disclosure. This embodiment may be suitable for improving the detection accuracy of the concentration of a tissue element to be detected. As shown in FIG. 18, a wearable apparatus 2 may include a body 20 and the non-invasive detection device 1 for tissue element according to the embodiments of the present disclosure. The non-invasive detection device 1 for tissue element may be provided on the body 20, and the non-invasive detection device 1 for tissue element may include a light source module 10, a detection module 11 and a processing module 12. The detection module 11 and the processing module 12 may be communicatively connected. The structure and the working principle thereof are described below in conjunction with the drawings.

The wearable apparatus 2 is worn on the detected site.

The light source module 10 may be configured to respectively emit the incident light of multiple predetermined wavelengths to the detected site.

The detection module 11 may be configured to obtain the light intensity values emitted from the surface of the detected site based on multiple photosensitive surfaces for each predetermined wavelength, and send each light intensity value to the processing module 12, multiple photosensitive surfaces are at a corresponding predetermined distance from the canter of the incident light, and the number of the predetermined distances is at least one.

The processing module 12 may be configured to determine the concentration of the tissue element to be detected according to light intensity values in each predetermined wavelength.

In the embodiment of the present disclosure, the non-invasive detection device 1 for tissue element may be disposed on the body 20. When the non-invasive detection device 1 for tissue element is needed for the tissue element detection, the wearable apparatus 2 may be worn on the detected site. Moreover, since the non-invasive detection device 1 for tissue element is used for detection, it is susceptible to the influence of the detection conditions, which thereby affects the detection accuracy. Therefore, in order to ensure a stability of the detection conditions and further improve the detection accuracy, the non-invasive detection device 1 for tissue element may be fixed so that a positional relationship between the detected site and the non-invasive detection device 1 for tissue element is a predetermined relationship. In the above, the position may be fixed by providing the non-invasive detection device 1 for tissue element on the body 20, which may ensure the stability of the detection conditions, and thereby improve the detection accuracy. In addition, the structure and the working principle of the non-invasive detection device 1 for tissue element may refer to the description of the non-invasive detection device 1 above, and will not be repeated here.

It should be noted that the wearable apparatus 2 may also include a display module, which may be communicatively connected with the processing module 12, the processing module 12 may send the concentration of the tissue element to be detected to the display module, and the display module may display the concentration of the tissue element to be detected, so that the detected individual may get the concentration of the tissue element to be detected through the display module. In addition, the wearable apparatus 2 may also include a voice module, which may be communicatively connected with the processing module 12. The processing module 12 may transmit the concentration of the tissue element to be detected to the voice module, and the voice module may generate voice instructions according to the concentration of the tissue element to be detected and play the voice instructions so that the detected individual may get the concentration of the tissue element to be detected.

The technical solution of the embodiment may realize a wide range of light intensity value reception, therefore, the light receiving efficiency is improved, and thus the detection accuracy of the tissue element to be detected is improved. Since the detection module may directly process the light intensity value emitted from the detected site, the light loss is reduced and the detection efficiency is improved. Due to a substantial reduction in the volume of the detection device, the detection device may be provided on the wearable apparatus, which may thereby be easily worn and fixed on the detected site, so that it may ensure the stability of the detection conditions, and correspondingly, improve the stability of the detection conditions. In addition, a portable detection is also realized. On this basis, since different light intensity values may be used for the differential operation, the common mode interference information may be eliminated, and therefore, the detection accuracy of the tissue element to be detected is also improved.

Figure 19:
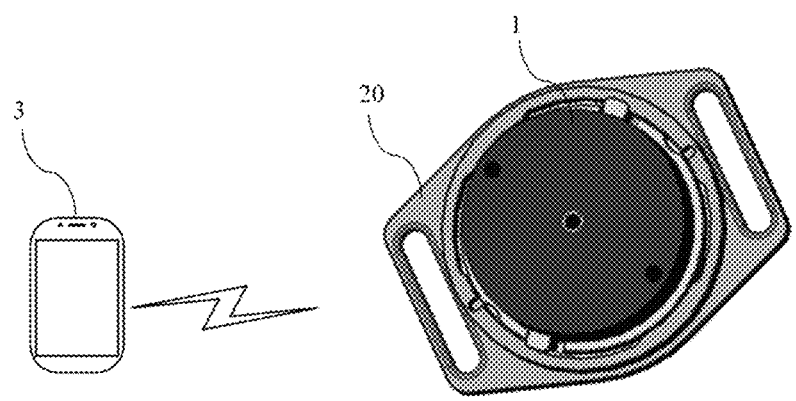
FIG. 19 is a schematic structural diagram of a non-invasive detection device for tissue element according to the embodiments of the present disclosure.

FIG. 19 is a schematic structural diagram of a non-invasive detection system for tissue element provided by the embodiments of the present disclosure. This embodiment may be suitable for improving the detection accuracy of the concentration of tissue element to be detected. As shown in FIG. 19, the non-invasive detection system for tissue element may include the wearable apparatus 2 according to the embodiments of the present disclosure and a terminal 3. The wearable apparatus may include a body 20 and a non-invasive detection device 1 for tissue element, the non-invasive detection device 1 for tissue element may be provided on the body 20. The non-invasive detection device 1 for tissue element may include a light source module 10, a detection module 11 and a processing module 12. The processing module 12 may be communicatively connected with the detection module 11 and the terminal 3, respectively. The structure and the working principle thereof are described below in conjunction with the drawings.

The wearable apparatus 2 is worn on the detected site.

The light source module 10 may be configured to respectively emit the incident light of multiple predetermined wavelengths to the detected site.

The detection module 11 may be configured to obtain the light intensity value emitted from the surface of the detected site based on multiple photosensitive surfaces for each predetermined wavelength, and emit each light intensity value to the processing module 12, multiple photosensitive surfaces are at a corresponding predetermined distance from the canter of the incident light, and the number of the predetermined distances is at least one.

The processing module 12 may be configured to process light intensity values in multiple predetermined wavelengths to obtain each processed light intensity values in multiple predetermined wavelengths, and emit light intensity values in multiple predetermined wavelengths to the terminal 3.

The terminal 3 is used to determine the concentration of the tissue element to be detected according to each process light intensity values in multiple predetermined wavelengths.

In the embodiment of the present disclosure, different from the above, in order to reduce a cost of the non-invasive detection device 1 for tissue element, the wearable apparatus 2 and the terminal 3 may be cooperated to determine the concentration of the tissue element to be detected. That is, the processing module 12 processes each light intensity value to obtain each processed light intensity value, and emits each processed light intensity value to the terminal 3. The terminal 3 may determine the concentration of the tissue element to be detected according to each processed light intensity value. Wherein, the processing operation of the processing module 12 for each light intensity value may include current-voltage conversion, amplification, and analog-to-digital conversion, etc. The terminal 3 may use the same method as the non-invasive detection method for tissue element according to the embodiments of the present disclosure, and determine the concentration of the tissue element to be detected according to each processed light intensity value, which is not repeated here. In addition, the structure and the working principle of the wearable apparatus 2 may refer to the description of the wearable apparatus 2 above, which is not repeated here.

It should be noted that, the terminal 3 may also display the concentration of the component to be detected, so that the detected individual may know the concentration of the tissue element to be detected. The terminal 3 may also generate voice instructions, which include the concentration of the tissue element to be detected, and plays the voice instructions so that the detected individual may know the concentration of the tissue element to be detected.

It should also be noted that in addition to using the terminal 3 to cooperate with the wearable apparatus 2 to determine the concentration of the tissue element to be detected, a cloud server and the wearable apparatus 2 may also be cooperated to determine the concentration of the tissue element to be detected.

The technical solution of this embodiment may achieve a wide range of light intensity value reception, therefore, the light receiving efficiency is improved, and thereby the detection accuracy of the tissue element to be detected is further improved. Since the detection module may directly process the light intensity value emitted from the detected site, the light loss is reduced and the detection efficiency is improved. Due to a substantial reduction in a volume of the detection device, the detection device may be provided on a wearable apparatus, which may thereby be easily worn and fixed on the detected site, which may ensure the stability of the detection conditions, and correspondingly, improve the stability of the detection conditions. In addition, a portable detection is also realized. On this basis, since different light intensity values may be used for the differential operation, the common mode interference information may be eliminated, and therefore, the detection accuracy of the tissue element to be detected is also improved.

The specific embodiments described above further describe the purpose, technical solutions and beneficial effects of the present disclosure in further detail. It should be understood that the above are only specific embodiments of the present disclosure and are not intended to limit the present disclosure. Within the spirit and principle of the present disclosure, any modification, equivalent replacement, improvement, etc., shall be included in the protection scope of the present disclosure.

What is claimed is:

1. A non-invasive detection method for tissue element, comprising:
    an emitting step, wherein incident light of multiple predetermined wavelengths is respectively emitted to a detected site;
    an obtaining step, wherein for each predetermined wavelength, light intensity values emitted from a surface of the detected site are obtained based on multiple photosensitive surfaces, and the multiple photosensitive surfaces of a detection module, are located at predetermined distances from a center of the incident light; and
    a determination step, wherein a concentration of tissue element to be detected is determined according to the light intensity values in the multiple predetermined wavelengths,
    wherein the method comprises:
    for each predetermined wavelength, obtaining the light intensity value emitted from the surface of the detected site based on M ring-shaped photosensitive surfaces, wherein each ring-shaped photosensitive surface corresponds to a light intensity value, M≥2, an inner diameter of each ring-shaped photosensitive surface is greater than or equal to 0.5 mm and less than or equal to 6 mm, and a ring width of each ring-shaped photosensitive surface is greater than or equal to 0.05 mm and less than or equal to 0.3 mm; and
    wherein the determination step comprises:
        for each predetermined wavelength,
        determining two light intensity values from the light intensity values in the predetermined wavelength;
        performing a differential operation on the two light intensity values to obtain a differential light intensity value in the predetermined wavelength; and
        determining the concentration of the tissue element to be detected according to differential light intensity values in the multiple predetermined wavelengths.

2. The method according to claim 1, wherein each predetermined wavelength is greater than or equal to 900 nm and less than or equal to 2400 nm.

3. The method according to claim 1, wherein
    the two light intensity values comprise a light intensity measurement value and a light intensity reference value.

4. The method according to claim 3, wherein the determining two light intensity values from the light intensity values in the predetermined wavelength comprises:
    for each predetermined wavelength, determining the light intensity measurement value and the light intensity reference value from the light intensity values corresponding to the predetermined wavelength according to predetermined conditions, wherein the predetermined conditions comprise at least one of a wavelength characteristic, an optical parameter and a skin structure parameter.

5. The method according to claim 4, wherein for each predetermined wavelength, the determining the light intensity measurement value and the light intensity reference value from the light intensity values corresponding to the predetermined wavelength according to predetermined conditions comprises:
    for each predetermined wavelength, according to a light intensity variation, determining the light intensity measurement value and the light intensity reference value from the light intensity values corresponding to the predetermined wavelength, wherein the light intensity measurement value is a light intensity value of which an absolute value of the light intensity variation is greater than or equal to a first variation threshold, the light intensity reference value is a light intensity value of which an absolute value of the light intensity variation is smaller than or equal to a second variation threshold, the light intensity variation is a variation between the light intensity value and corresponding predetermined light intensity value, the first variation threshold is greater than the second variation threshold, and the predetermined light intensity value is the light intensity value emitted from the surface of the detected site when the concentration of the tissue element to be detected is a predetermined concentration.

6. A non-invasive detection device for tissue element, comprising: a light source module, a detection module and a processing module; the detection module is in communication with the processing module;
    wherein the light source module is configured for respectively emitting incident light of multiple predetermined wavelengths to a detected site;
    the detection module is configured to obtain, for each predetermined wavelength, light intensity values emitted from a surface of the detected site based on multiple photosensitive surfaces of the detection module, and to send the light intensity values to the processing module, wherein the multiple photosensitive surfaces are located at predetermined distances from a center of the incident light, and there are at least one predetermined distances; and
    the processing module is configured for determining the concentration of a tissue element to be detected according to the light intensity values in the multiple predetermined wavelengths, wherein the detection module being configured to obtain, for each predetermined wavelength, light intensity values emitted from a surface of the detected site based on multiple photosensitive surfaces of a detection module comprises:

M ring-shaped photosensitive surfaces of the detection module, wherein each ring-shaped photosensitive surface corresponds to a light intensity value, M≥2, an inner diameter of each ring-shaped photosensitive surface is greater than or equal to 0.5 mm and less than or equal to 6 mm, and a ring width of each ring-shaped photosensitive surface is greater than or equal to 0.05 mm and less than or equal to 0.3 mm; and wherein the processing module being configured to determine a concentration of the tissue element to be detected according to the light intensity values in the multiple predetermined wavelengths is configured to:

for each predetermined wavelength,
determine two light intensity values from the light intensity values in the predetermined wavelength;
perform a differential operation on the two light intensity values to obtain a differential light intensity value in the predetermined wavelength; and
determine the concentration of the tissue element to be detected according to differential light intensity values in the multiple predetermined wavelengths.

7. The device according to claim 6, wherein different ring-shaped photosensitive surfaces are provided with a same geometric center.

8. The device according to claim 6, further comprising a first sleeve; the first sleeve is provided on an upper surface of the detection module, and an inner diameter of the first sleeve is greater than a diameter of an aperture on the detection module; and the first sleeve is configured for preventing surface reflected light that is generated by incident light passing through the surface of the detected site from entering the detection module, and, preventing diffracted light that is generated by incident light passing through the aperture of the detection module from entering the detection module; and/or wherein the detection module is further provided with a second sleeve connected integrally; the second sleeve is provided on an upper surface of the detection module, and an inner diameter of the second sleeve is greater than a diameter of an aperture on the detection module; and the second sleeve is configured for preventing surface reflected light that is generated by incident light passing through the surface of the detected site from entering the detection module, and preventing diffracted light that is generated by incident light passing through the aperture of the detection module from entering the detection module; and/or, wherein the device further comprises a third sleeve, an upper surface of the third sleeve passes through an aperture of the detection module, and exceeds an upper surface of the detection module; and the third sleeve is configured for preventing surface reflected light that side generated by incident light passing through the surface of the detected site from entering the detection module, and preventing diffracted light that is generated by incident light passing through the aperture of the detection module from entering the detection module.

9. The device according to claim 6, further comprising a housing; wherein the light source module, the detection module and the processing module are provided inside the housing, and an upper surface of the detection module is lower than an upper surface of the housing.

10. The device according to claim 9, further comprising a protection member; wherein the protection member is provided at an aperture of the upper surface of the housing, and an upper surface of the protection member is lower than the upper surface of the housing, the protection member is provided with an aperture, and has a same geometric center with the housing; a light transmittance of the protection member is greater than or equal to a light transmittance threshold; the protection member is configured for protecting the detection module, and, when the non-invasive detection device for tissue element is worn to the detected site, ensuring that a skin condition of the detected site remains in a natural state and realizing a non-contact detection.

11. The device according to claim 9, further comprising a contact member; wherein the contact member is provided on the upper surface of the housing, and a thermal conductivity of material of the contact member is within a range of air thermal conductivity;

the contact member is configured for ensuring that a skin condition of the detected site is remained in a natural state and realizing a non-contact detection when the non-invasive detection device for tissue element is worn to the detected site, and shortening a time for a thermal conduction between the non-invasive detection device when it is worn to the detected site and the detected site to reach a thermal equilibrium state by setting the thermal conductivity of the material of the contact member within the range of air thermal conductivity.

12. The device according to claim 11, wherein the upper surface of the housing is plated with a heat-insulating material, and the thermal conductivity of the heat-insulating material is within the range of air thermal conductivity;

the heat-insulating material is configured for ensuring that the skin condition of the detected site is remained in the natural state and realizing a non-contact detection when the non-invasive detection device for tissue element is worn to the detected site, and shortening a time for a thermal conduction between the non-invasive detection device when it is worn to the detected site and the detected site to reach a thermal equilibrium state by setting the thermal conductivity of the heat-insulating material within the range of air thermal conductivity.

13. The device according to claim 6, wherein the light source module further comprises a light source emitting unit or an incident optical fiber.

14. A wearable apparatus, comprising: a body and the non-invasive detection device for tissue element according to claim 6;

wherein the non-invasive detection device for tissue element is provided on the body; and the wearable apparatus is configured to be worn to a detected site.

* * * * *